US012559788B2

(12) United States Patent
Lebofsky et al.

(10) Patent No.: US 12,559,788 B2
(45) Date of Patent: Feb. 24, 2026

(54) MULTIPLE BEADS PER DROPLET RESOLUTION

(71) Applicant: Bio-Rad Laboratories, Inc., Hercules, CA (US)

(72) Inventors: Ronald Lebofsky, Kensington, CA (US); Zachary Burkett, Walnut Creek, CA (US); Man Cheng, Danville, CA (US); Meiye Wu, Tracy, CA (US); Pranav Patel, Fremont, CA (US); Duc Do, San Jose, CA (US); Arkadiusz Bibillo, Walnut Creek, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 407 days.

(21) Appl. No.: 16/896,118

(22) Filed: Jun. 8, 2020

(65) Prior Publication Data

US 2020/0385791 A1      Dec. 10, 2020

Related U.S. Application Data

(60) Provisional application No. 62/861,959, filed on Jun. 14, 2019, provisional application No. 62/858,940, filed on Jun. 7, 2019.

(51) Int. Cl.

| | |
|---|---|
| *C12Q 1/6834* | (2018.01) |
| *C12N 15/10* | (2006.01) |
| *C12Q 1/6874* | (2018.01) |
| *C12Q 1/6876* | (2018.01) |

(52) U.S. Cl.
CPC ....... *C12Q 1/6834* (2013.01); *C12N 15/1065* (2013.01); *C12Q 1/6874* (2013.01); *C12Q 1/6876* (2013.01); *C12Q 2563/185* (2013.01)

(58) Field of Classification Search
CPC .. C12Q 1/6834; C12Q 1/6874; C12Q 1/6876; C12Q 2563/185; C12Q 1/6806; C12N 15/1065; C12N 15/1075
See application file for complete search history.

(56) References Cited

U.S. PATENT DOCUMENTS

| | | | |
|---|---|---|---|
| 2006/0281079 A1* | 12/2006 | Eickbush ............. | C12N 9/1276 435/6.13 |
| 2009/0035777 A1 | 2/2009 | Kokoris et al. | |
| 2011/0028334 A1 | 2/2011 | Hayden | |
| 2012/0034603 A1 | 2/2012 | Oliphant et al. | |
| 2016/0312276 A1* | 10/2016 | Fu ........................ | C12Q 1/6806 |
| 2017/0232417 A1* | 8/2017 | Lebofsky ............. | C12Q 1/6806 506/16 |
| 2019/0241944 A1 | 8/2019 | Cater et al. | |

FOREIGN PATENT DOCUMENTS

| | | | | |
|---|---|---|---|---|
| WO | 0220541 A2 | 3/2002 | | |
| WO | 2004058794 A1 | 7/2004 | | |
| WO | 2011/056866 A2 | 5/2011 | | |
| WO | 2015200541 A1 | 12/2015 | | |
| WO | WO-2017079593 A1 * | 5/2017 | ......... | C12N 15/1065 |
| WO | 2017120531 A1 | 7/2017 | | |
| WO | WO-2018017914 A1 * | 1/2018 | .......... | C12Q 1/6804 |
| WO | 2018140966 A1 | 8/2018 | | |
| WO | 2018172726 A1 | 9/2018 | | |
| WO | 2019032760 A1 | 2/2019 | | |
| WO | 2019/099751 A1 | 5/2019 | | |

OTHER PUBLICATIONS

Griebel (Nucleic Acids Research, 2012, vol. 40, No. 20 10073-10083).*

Moss (RNA Biology 8:5, 714-718; September/October).*

International Search Report and Written Opinion mailed Oct. 26, 2020 in PCT Appln. PCT/US2020/036699; 23 pages.

Gerard, et al.; "Reverse Transcriptase (EC 2.7.7.49)" Chapter 6 from *Methods in Molecular Biology*; vol. 16: Enzymes of Molecular Biology; Edited by M.M. Burell; Humana Press, Inc.; Totowa, NJ; 1993; pp. 73-93.

International Search Report and Written Opinion in PCT/US2019/015638 mailed Jul. 5, 2019; 15 pages.

Lan, F. et al.; "Droplet barcoding for massively parallel single-molecule deep sequencing"; *Nature Communications*; vol. 7, No. 11784; Jun. 29, 2016; pp. 1-10.

Richard T Pon et al, "Tandem Oligonucleotide Synthesis Using Linker Phosphoramidites", Nucleic Acids Research, Oxford University Press, GB, (Jan. 1, 2005), vol. 33, No. 6, doi:10.1093/NAR/GKI333, ISSN 0305-1048, pp. 1940-1948, XP002428185.

* cited by examiner

*Primary Examiner* — Steven Pohnert
(74) *Attorney, Agent, or Firm* — Thomas C. Meyers; Sullivan & Worcester LLP

(57) ABSTRACT

Provided are methods for detecting the presence of multiple barcoded solid supports in partitions, the method comprising providing a plurality of partitions wherein at least some partitions comprises multiple solid supports, where each solid support is linked to different solid support oligonucleotides, the solid support oligonucleotides comprising a barcode unique for the solid support; synthesizing a complementary sequence of the oligonucleotides to produce a double-stranded polynucleotide having barcodes from two of the solid support oligonucleotides; and sequencing one or both strands of the double-stranded polynucleotides, wherein sequences comprising two different barcodes indicates the presence of two solid supports in the same partition. Also provided are compositions and methods for producing the oligonucleotides.

9 Claims, 17 Drawing Sheets

Specification includes a Sequence Listing.

READ 1

@NS500711:125:HYVCKBGX5:1:11101:13450:19351 1:N:0:ACTCGCTA
TAGCCAATCTGAACGCCTATGCATGACAACCACACAGTCAGTCACGGCTGCTT

+

AAAAAEEEEEEEEEEEEEE/EEAEE/EEAEEE/EEE<EEAEEEEEE/E///

READ 2

@NS500711:125:HYVCKBGX5:1:11101:13450:19351 2:N:0:ACTCGCTA
CGCGGGAATTCTGAACGCCTATGCATGACAACCACACAGTCAGTCAAGGCTTCTTTTTTTTTTTTTTTTTTTTT

+

A/A<AEEEAEA//EAEAEEE</EEE////EAEEE/E///</E//A<////</AE/EAAEE/EEA/E<A<EE/</</

From the following barcode scheme...

NNNNNNXXXXXNVGCTATGCATGACXXXXXXCAGTCAXXXXXXTTTTT......

| UMI | BC1 | Phase blocks | Linker 1 | BC2 | Linker 2 | BC3 | PolyT |
|-----|-----|--------------|----------|-----|----------|-----|-------|

*FIG. 4*

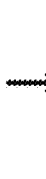
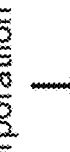
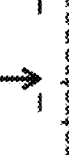
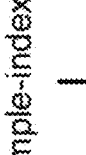

1. Partitioning of single-cell and multiple barcode-beads.

2. Cell-lysis, bead oligos cleavage, RNA fragmentation and RNA capture, Barcode-joining and R1/R2 sequence adapters incorporation 3. Partition breakage, magnetic beads pull down, and washing 4. R2 retrotransposase mediated cDNA synthesis and 3' adaptor add-on 5. Sample-indexing 6. Library size-selection, Purification, Sequencing, and bioinformatic analysis Cell Partiton (droplet)

Barcode-bead

*FIG. 7*

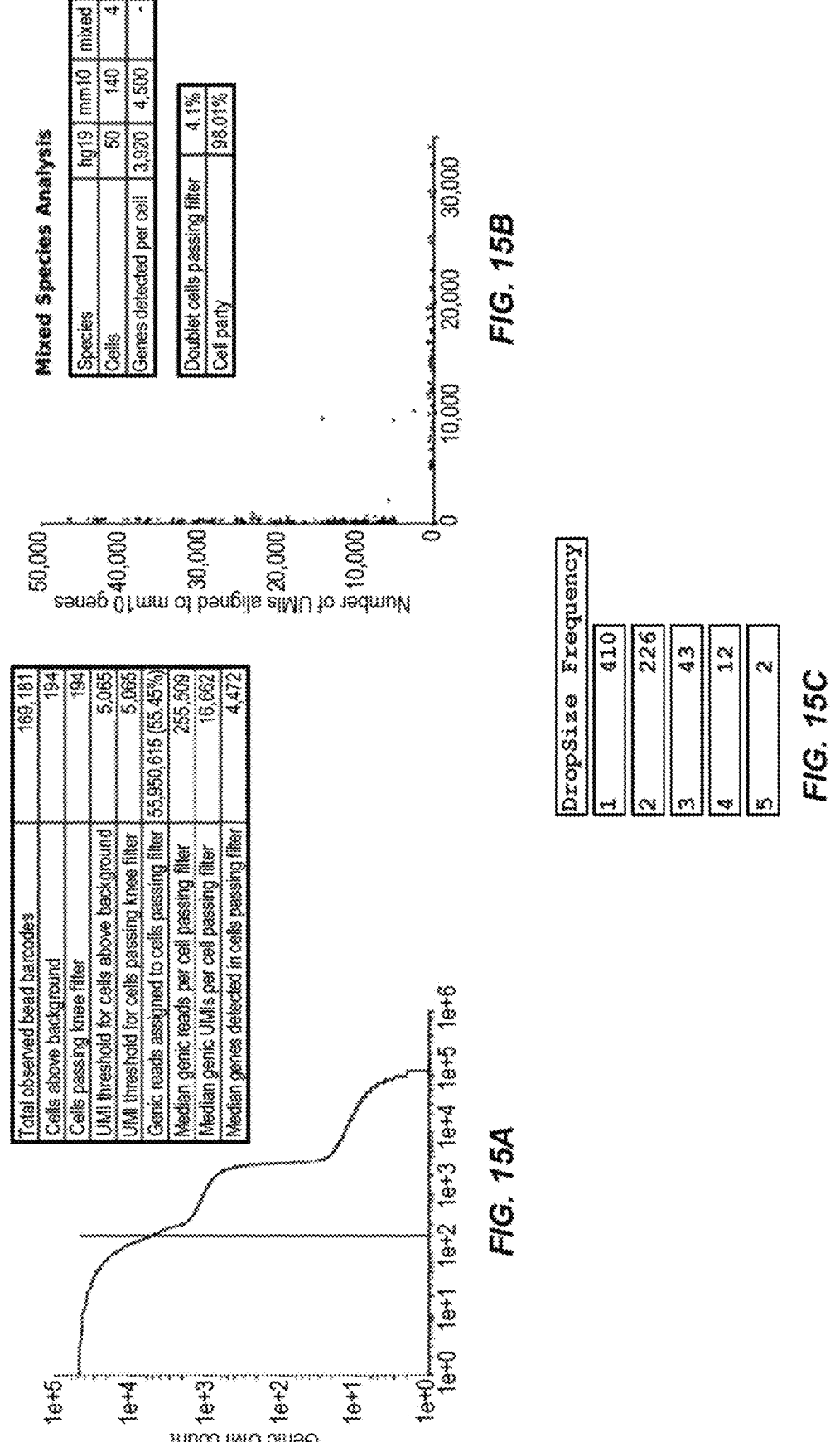

Mixed Species Analysis

| Species | hg19 | mm10 | mixed |
|---|---|---|---|
| Cells | 50 | 140 | 4 |
| Genes detected per cell | 3,920 | 4,580 | - |

| Doublet cells passing filter | 4.1% |
|---|---|
| Cell purity | 98.01% |

*FIG. 15B*

| | |
|---|---|
| Total observed bead barcodes | 169,181 |
| Cells above background | 194 |
| Cells passing knee filter | 194 |
| UMI threshold for cells above background | 5,065 |
| UMI threshold for cells passing knee filter | 5,065 |
| Genic reads assigned to cells passing filter | 55,950,615 (55.45%) |
| Median genic reads per cell passing filter | 255,509 |
| Median genic UMIs per cell passing filter | 16,662 |
| Median genes detected in cells passing filter | 4,472 |

*FIG. 15A*

| DropSize | Frequency |
|---|---|
| 1 | 410 |
| 2 | 226 |
| 3 | 43 |
| 4 | 12 |
| 5 | 2 |

Figure 16:
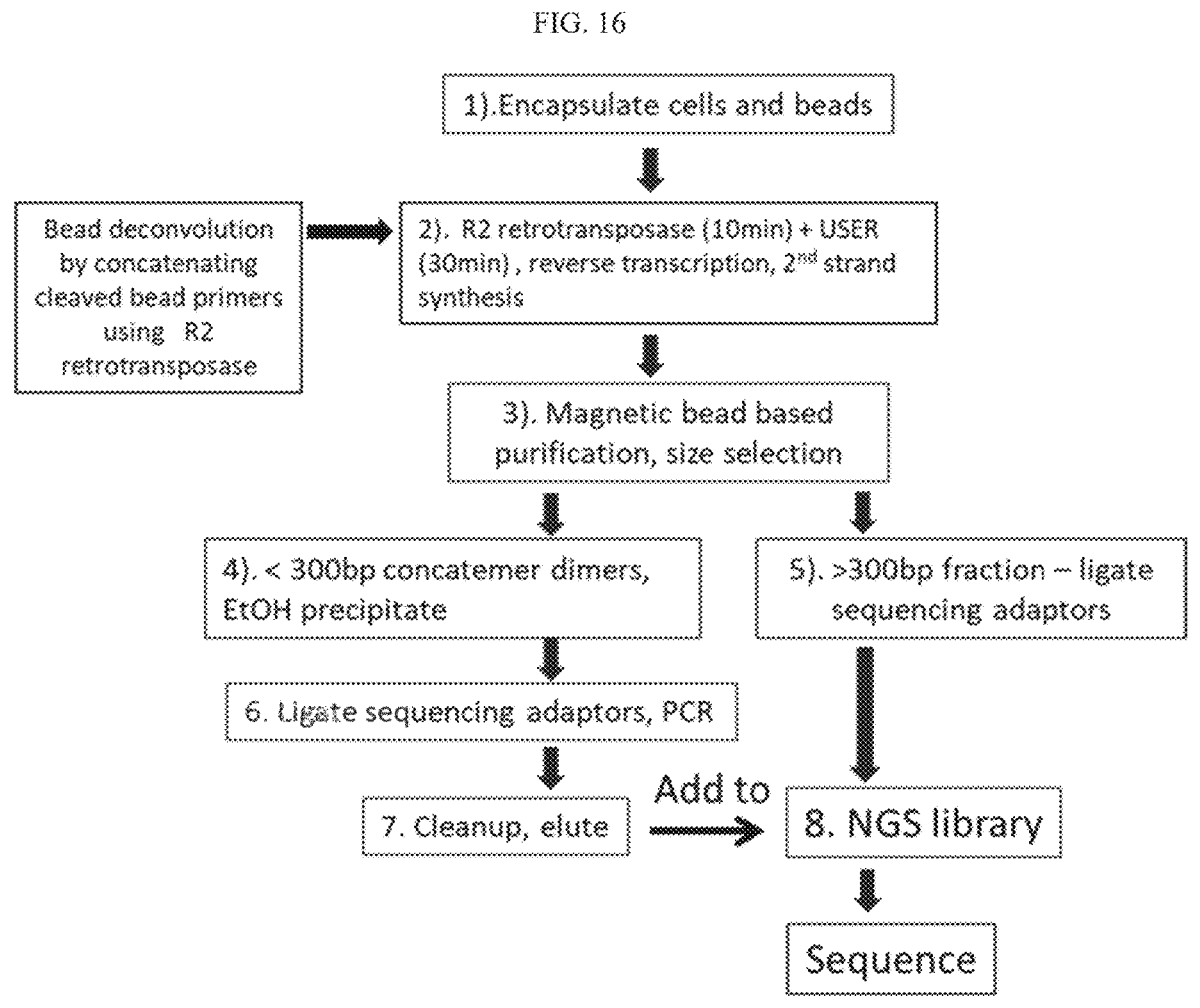

1).Encapsulate cells and beads

Bead deconvolution
by concatenating
cleaved bead primers
using R2
retrotransposase 2). R2 retrotransposase (10min) + USER
(30min) , reverse transcription, 2$^{nd}$ strand
synthesis 3). Magnetic bead based
purification, size selection 4). < 300bp concatemer dimers,
EtOH precipitate 5). >300bp fraction – ligate
sequencing adaptors 6. Ligate sequencing adaptors, PCR 7. Cleanup, elute Add to 8. NGS library Sequence

1

MULTIPLE BEADS PER DROPLET RESOLUTION

CROSS-REFERENCES TO RELATED APPLICATIONS

The present application claims the benefit of U.S. Provisional Appln. No. 62/858,940 filed Jun. 7, 2019, and U.S. Provisional Appln. No. 62/861,959 filed Jun. 14, 2019, the full disclosures of which are incorporated herein by reference in their entireties for all purposes.

REFERENCE TO A "SEQUENCE LISTING," A TABLE, OR A COMPUTER PROGRAM LISTING APPENDIX SUBMITTED AS AN ASCII TEXT FILE

The Sequence Listing written in file 094848-1190274-116910US_SL.TXT, created on Jun. 4, 2020, 2,812 bytes, machine format IBM-PC, MS-Windows operating system, is hereby incorporated by reference in its entirety for all purposes.

BACKGROUND OF THE INVENTION

Tagging biological substrates with molecular barcodes in partitions can provide novel biological insight of the substrates that co-localize to discrete partitions, through the sequencing of the molecular barcodes and analysis, thereof. Increasing the number of barcoding competent partitions, such as droplets, increases the number of sequencing based data points and converts a greater fraction of input substrates into data. Barcodes can be delivered to partitions, such as droplets, using beads as the delivery vehicle. Thus, barcode bead overloading in partitions, which results in partitions with more than one bead and increases the percentage of barcoding competent partitions, provides higher substrate to sequencing data conversion rates. However, when two or more barcodes occur in discrete partitions, the substrates and data are split between the two barcodes, creating fractionated data points. The instant disclose provides a solution to the problems created when more than one barcoded bead is present in a partition, such as problems associated with fractionated data points.

BRIEF SUMMARY OF THE INVENTION

Described herein are methods for detecting the presence of multiple barcoded solid supports in partitions, compositions comprising barcoded solid supports, and methods for producing the barcoded solid supports.

In one aspect, the methods comprise, in the following order:

a) providing a plurality of partitions wherein at least some partitions comprises multiple solid supports, each solid support linked to different solid support oligonucleotides, the solid support oligonucleotides comprising a barcode unique for the solid support;

b) synthesizing a complementary sequence of the oligonucleotides to produce a double-stranded polynucleotide having barcodes from two of the solid support oligonucleotides;

c) sequencing one or both strands of the double-stranded polynucleotides, wherein sequences comprising two different barcodes indicates the presence of two solid supports in the same partition in the providing step.

In some embodiments, the solid support oligonucleotides comprising barcodes are cleaved from the solid supports, for example, between steps a) and b). In some embodiments, step b) occurs inside the partition. In some embodiments, the method further comprises combining the contents of the partitions after step b). In some embodiments, step b) occurs outside the partition.

In some embodiments, step b) comprises contacting the solid support oligonucleotides with a R2 retrotransposase. In some embodiments, step b) comprises contacting the solid support oligonucleotides with a reverse transcriptase. In some embodiments, step b) comprises contacting the solid support oligonucleotides with a DNA polymerase.

In some embodiments, double stranded adapters are added to the double-stranded polynucleotide. In some embodiments, the double stranded adapters are added by contacting the double-stranded polynucleotide with an adapter-loaded transposase or tagmentase.

In some embodiments, the second barcode sequence is added by a single stranded ligase.

In some embodiments, step b) is template independent.

In some embodiments, the solid support oligonucleotides further comprise a universal primer binding sequence.

In some embodiments, the partitions are droplets in an emulsion.

In some embodiments, the solid support oligonucleotides are attached to sample nucleic acid sequences. The sample nucleic acid sequences can be RNA, mRNA, or DNA.

In some embodiments, the sample nucleic acid sequences are derived from a single cell.

In some embodiments, the solid support oligonucleotides further comprise a capture sequence, the partitions further comprise a detector oligonucleotide having a 3' end complementary to the capture sequence and a 5' palindromic sequence, and the method further comprises:

d) in the partitions, hybridizing the capture sequence of some of the solid support oligonucleotides to the 3' ends of detector oligonucleotides in the presence of a polymerase to generate extended solid support oligonucleotides that comprise a complement of the detector oligonucleotide, wherein the extended detector solid support oligonucleotides comprise a 3' end that is complementary to the palindromic sequence; and e) in the partitions, hybridizing 3' ends of the extended solid support oligonucleotides and extending the 3' ends of the extended detector solid support oligonucleotides with the polymerase, thereby forming double-stranded polynucleotides having barcodes from two of the solid support oligonucleotides.

In some embodiments, the ratio of solid support oligonucleotides to detector oligonucleotides is at least 5:1 to 100,000:1.

In some embodiments, at least some solid support oligonucleotide capture sequences are hybridized to sample nucleic acids and are extended by the polymerase to generate extended sample solid support oligonucleotides that comprise a complement of a sample nucleic acid. The sequencing can comprise sequencing the extended sample solid support oligonucleotides to generate sequencing reads having a solid support barcode and a sample nucleic acid sequence.

In some embodiments, the method further comprises deconvoluting the sequencing reads by partition, wherein two different sequencing reads having two different barcodes are considered to be from the same partition if a sequence read comprises the two different barcodes.

In any of the embodiments described herein, the palindromic sequence can be between 4 and 250 nucleotides long, including any range of integer values between 4 and 250 nucleotides in length, such as a range from 4, 5, 6, 7, 8, 9, or 10 nucleotides to 20, 30, 40, 50, 60, 70, 80, 90, 100, 150, 200 or 250 nucleotides in length, such as 10 to 20, 10 to 30, 20 to 30, or 20 to 40 nucleotides in length. In some embodiments, the palindrome sequence comprises a region of 10-20 nucleotides and a region comprising the reverse complement thereof, such that the total length of the palindrome sequence is 20-40 nucleotides in length.

In any of the embodiments described herein, the barcodes can be 4 to 250 nucleotides long, including any range of integer values between 4 and 250 nucleotides in length, such as a range from 4, 5, 6, 7, 8, 9, or 10 nucleotides to 20, 30, 40, 50, 60, 70, 80, 90, 100, 150, 200 or 250 nucleotides in length.

In some embodiments, the double-stranded polynucleotides having barcodes are cleaved from the solid supports between steps e) and f).

In some embodiments, the solid support oligonucleotides are linked to the solid support via a uracil base and the method comprises: contacting the solid support oligonucleotides solid support oligonucleotides with UDGase, thereby cleaving the solid support oligonucleotides from the solid support.

In some embodiments, the solid support oligonucleotides comprise one or more biotin or biotin analogs and the method comprises: purifying cleaved solid support oligonucleotides by binding the cleaved solid support oligonucleotides to a streptavidin-linked solid support and washing non-binding components from the streptavidin-linked solid support; and eluting the cleaved solid support oligonucleotides.

In some embodiments, the streptavidin-linked solid support is a magnetic or paramagnetic bead.

In some embodiments, step e) comprises 2-5 cycles of polymerase chain reaction (PCR).

In some embodiments, the solid supports are beads.

In another aspect, a method for producing a solid support attached to two or more different oligonucleotides is described, the method comprising attaching a first oligonucleotide to the solid support, wherein the first oligonucleotide comprises a barcode unique for the solid support, a capture sequence, and a sequencing adaptor;

attaching a second oligonucleotide to the solid support, wherein the second oligonucleotide comprises a barcode unique for the solid support, a sequencing adaptor, and a palindrome sequence at the 3' end.

In some embodiments, the oligonucleotide is chemically conjugated to the solid support.

In some embodiments, the oligonucleotide is non-covalently attached to the solid support.

In another aspect, a composition is provided, the composition comprising a partition comprising two or more solid supports attached to an oligonucleotide comprising a barcode sequence, where each solid support is linked or attached to a different oligonucleotide, and the oligonucleotide comprises a barcode unique for the solid support to which it is attached.

In another aspect, a method for producing a library of nucleic acid molecules for sequencing is described, the method comprising:

a) providing a plurality of partitions wherein at least some partitions comprise a single cell and multiple solid supports, where different solid supports are linked to first and second solid support oligonucleotides in the same partition, the first solid support oligonucleotides comprising a barcode unique for the solid support, a capture sequence, and a sequencing adaptor, and the second solid support oligonucleotides comprise the barcode unique for the solid support, a sequencing adaptor, and a palindrome sequence at the 3' end;

b) releasing the oligonucleotides from the solid supports and hybridizing the RNA fragments to the capture sequence of one or more first oligonucleotides to form RNA/oligonucleotide hybrids;

c) hybridizing the second solid support oligonucleotides comprising the palindrome sequence to each other;

d) extending the hybridized oligonucleotides to form double stranded DNA dimer molecules comprising a first and second barcode, where the first and second barcodes are from the same or different solid support oligonucleotides in the same partition;

e) amplifying the DNA molecules to produce a library of nucleic acid molecules;

f) releasing the contents of the partitions, and contacting the RNA hybridized to the first oligonucleotides with R2 retrotransposase to synthesize cDNA in the presence of an acceptor template to add a 3' adaptor sequence;

g) amplifying the first oligonucleotides comprising cDNA and the 3' adaptor to generate a cDNA library comprising adaptor sequences; and h) sequencing the nucleic acid molecules in the library of step (g) and (i), wherein sequences comprising the same barcodes indicates the solid supports were present in the same partition.

In some embodiments, the first and second solid support oligonucleotides comprise or are attached to the same unique barcode sequence.

In some embodiments, the method further comprises lysing the cell to release RNA.

In some embodiments, the method further comprises fragmenting the RNA to produce RNA fragments.

In some embodiments, the partitions comprise a DNA polymerase, divalent ions, sequencing adaptors, deoxynucleotide triphosphates (dNTPs), and primers having at least a 3' sequence complementary to the sequencing adaptors. In some embodiments, the partition further comprises poly(A) polymerase and ATP, and a poly-A tail is added to the RNA fragments.

In some embodiments, the first and/or second solid support oligonucleotide comprises a uracil base, and the oligonucleotide is released from the solid support by contacting the oligonucleotide with a UDGase or USER enzyme.

In some embodiments, step (g) comprises melting the double stranded DNA molecules and hybridizing primers to the sequencing adaptors, extending the primers using a polymerase, and amplifying the extended molecule by PCR.

In some embodiments, the capture sequence comprises poly dT, a random sequence, or a gene-specific sequence.

In some embodiments, the partition is a droplet in an emulsion or a microwell.

In another aspect, a solid support is provided, the solid support linked to (i) a plurality of first solid support oligonucleotides comprising a barcode sequence unique for the solid support and a capture sequence; and (ii) a plurality of second oligonucleotides having a 3' end comprising a sequence complementary to the capture sequence, the barcode sequence, and a 5' palindromic sequence;

wherein the ratio of first solid support oligonucleotides to second oligonucleotides is at least 5:1, 10:1, 100:1, 1000:1, 5000:1, 10000:1, 20000:1; 30000:1. 40000:1, 50000:1; 60000:1, 70000:1; 80000:1, 90000:1, or 100000:1.

In some embodiments, the palindromic sequence can be between 4 and 250 nucleotides long, including any range of integer values between 4 and 250 nucleotides in length, such as a range from 4, 5, 6, 7, 8, 9, or 10 nucleotides to 20, 30, 40, 50, 60, 70, 80, 90, 100, 150, 200 or 250 nucleotides in length, such as 10 to 20, 10 to 30, 20 to 30, or 20 to 40 nucleotides in length. In some embodiments, the palindrome sequence comprises a region of 10-20 nucleotides and a region comprising the reverse complement thereof, such that the total length of the palindrome sequence is 20-40 nucleotides in length. In some embodiments, the barcodes can be 4 to 250 nucleotides long, including any range of integer values between 4 and 250 nucleotides in length, such as a range from 4, 5, 6, 7, 8, 9, or 10 nucleotides to 20, 30, 40, 50, 60, 70, 80, 90, 100, 150, 200 or 250 nucleotides in length.

In some embodiments, the first oligonucleotide further comprises one or more of: a) a uracil base; b) a biotin base; or d) an adapter sequence for sequencing reactions.

In another aspect, a partition comprising two or more solid supports described herein is provided, wherein each solid support is linked to different solid support oligonucleotides comprising different barcode sequences unique for the solid support.

In another aspect, a kit comprising a solid support described herein is provided. In some embodiments, the kit comprises instructions for use.

In another aspect, a method of detecting the presence of multiple barcoded solid supports in partitions is described, the method comprising:

a) providing a plurality of partitions wherein at least some partitions comprise multiple solid supports, where each solid support is linked to (i) a plurality of first solid support oligonucleotides comprising a barcode sequence unique for the solid support and a capture sequence; and (ii) one or more second oligonucleotides having a 3' end comprising a sequence complementary to the capture sequence, the barcode sequence and a 5' palindromic sequence; wherein the ratio of first solid support oligonucleotides to second oligonucleotides is at least at least 5:1, 10:1, 100:1, 1000:1, 5000:1, 10000:1, 20000:1; 30000:1. 40000:1, 50000:1; 60000:1, 70000:1; 80000:1, 90000:1, or 100000:1;

b) releasing the first and second oligonucleotides from the solid supports;

c) hybridizing the capture sequence of some of the solid support oligonucleotides to the 3' ends of the second oligonucleotides in the presence of a first polymerase to generate extended solid support oligonucleotides that comprise a complement of the second oligonucleotide, wherein the extended solid support oligonucleotides comprise a 3' end that d) hybridizing the 3' ends of the extended solid support oligonucleotides and extending the 3' ends with a second polymerase, thereby forming double-stranded polynucleotides having barcodes from two of the solid support oligonucleotides.

e) sequencing one or both strands of the double-stranded polynucleotides, wherein sequences comprising two different barcodes indicates the presence of two solid supports in the same partition.

In some embodiments, the sequence complementary to the capture sequence comprises a 3' terminator or is blocked at the 3' end to prevent extension by a polymerase.

In some embodiments, the first polymerase in step (c) does not have exonuclease activity. In some embodiments, the polymerase is a Therminator™ DNA polymerase or a Taq DNA polymerase.

In some embodiments, the first oligonucleotide further comprises one or more of: a) a uracil base; b) a biotin base; or d) an adapter sequence for sequencing reactions.

In some embodiments, the partition is a droplet in an emulsion or a microwell.

In another aspect, a method for producing a solid support linked to an oligonucleotide is described, the method comprising:

i) providing a solid support linked to a plurality of first solid support oligonucleotides, the first oligonucleotides comprising a barcode sequence unique for the solid support and a 3' capture sequence;

ii) hybridizing the 3' capture sequence of some of the solid support oligonucleotides to a second oligonucleotide having a 3' end comprising a sequence complementary to the capture sequence, and a 5' palindromic sequence, wherein the ratio of first solid support oligonucleotides to second oligonucleotide is at least 5:1, 10:1, 100:1, 1000:1, 5000:1, 10000:1, 20000:1; 30000:1. 40000:1, 50000:1; 60000:1, 70000:1; 80000:1, 90000:1, or 100000:1;

iii) extending the first solid support oligonucleotides with a polymerase to generate extended solid support oligonucleotides that comprise a complement of the second oligonucleotide and a 3' end that is complementary to the palindromic sequence;

thereby producing the solid support.

In some embodiments, the second oligonucleotides are removed by denaturation and washing.

In some embodiments, the first oligonucleotides comprise a uracil base 5' of the barcode sequence, and the extended solid support oligonucleotides from step (iii) are released from the solid support by UDGase, and the second oligonucleotides are removed by denaturation during the first amplification cycle. In some embodiments, the denaturation occurs inside a partition.

BRIEF DESCRIPTION OF THE DRAWINGS

FIG. 4 shows a representative example of sequence generated from reverse transcriptase synthesis of chimeric bead oligo sequences, as shown in FIG. 3. Examples of sequences generated from chimeric sequence produced from reverse transcription reaction performed using gel beads on the ddSEQ machine. Bead oligo barcodes are generated from the combination of barcode (BC) 1, BC2, and BC3. Two different bead barcode oligo sequences are found in read 1 and read 2 respectively. This information from the same read or cluster in an Illumina flow cell co-localizes the relevant beads underlying the barcode sequences to the same partition during the barcode reaction. FIG. 4 discloses SEQ ID NOS 7-9, respectively, in order of appearance.

FIG. 7 illustrates the steps of another embodiment described herein. A partition is loaded with one cell and various amounts of barcode-beads by a microfluidic system. The cell is then lysed and barcode oligos are released from carrier beads by enzymatic cleavage within each partition. RNA molecules released from cell lysis are fragmented and then poly-A tailed RNA fragments are captured by the barcode-oligos "a". The barcode oligos "b" that originated from different or the same carrier beads hybridize to each other randomly and are subsequently extended by DNA polymerase to form inter- and intra-molecular barcode-dimers. Following partition breakage, the RNA/barcode-oligo hybrids and the barcode-dimers are pulled down by the magnetic beads. After washing, cDNA synthesis and 3'-adaptor addition are carried out through the reverse-transcription and the add-on-adaptor processes using R2 retrotransposase. The resulting library of barcode-dimers and cDNA is indexed, size selected, and purified before next-generation sequencing, and the sequences are analyzed by bioinformatics.

FIG. 12A represents de-barcoded data; barcodes above the knee to the left of the vertical blue line are beads in droplets containing cells. The selected barcodes are processed to determine the co-localization of beads in a droplet. Bead/s determined to be in the same droplet are merged and assigned a "cell barcode". FIG. 12B shows the cell barcode of merged bead/s with detected unique transcripts per cell (UMIs); barcodes above the knee to the left of the heavy vertical line are called and filtered as cells in the sample.

FIG. 15A shows the unique genic UMI per bead barcode is plotted against each barcode in rank-descending order by unique genic UMI count. FIG. 15B shows a plot of mouse genes aligning to MM10 (red) versus human genes aligning to hg19 (blue). FIG. 15C shows a Table of detected droplets containing multiple barcodes. If only one BC flanking the polyT motif was detected, the DropSize is assigned 1; two BC is Dropsize of 2 and so on. The frequency is how many times each droplet size appears in the library. Total of 693 droplets were constructed from R2 retrotransposase concatemers in library without bead overloading.

FIG. 16 illustrates a workflow involving R2 retrotransposase to generate heterodimers in a 3'WTA library for bead deconvolution.

DEFINITIONS

Figure 1:
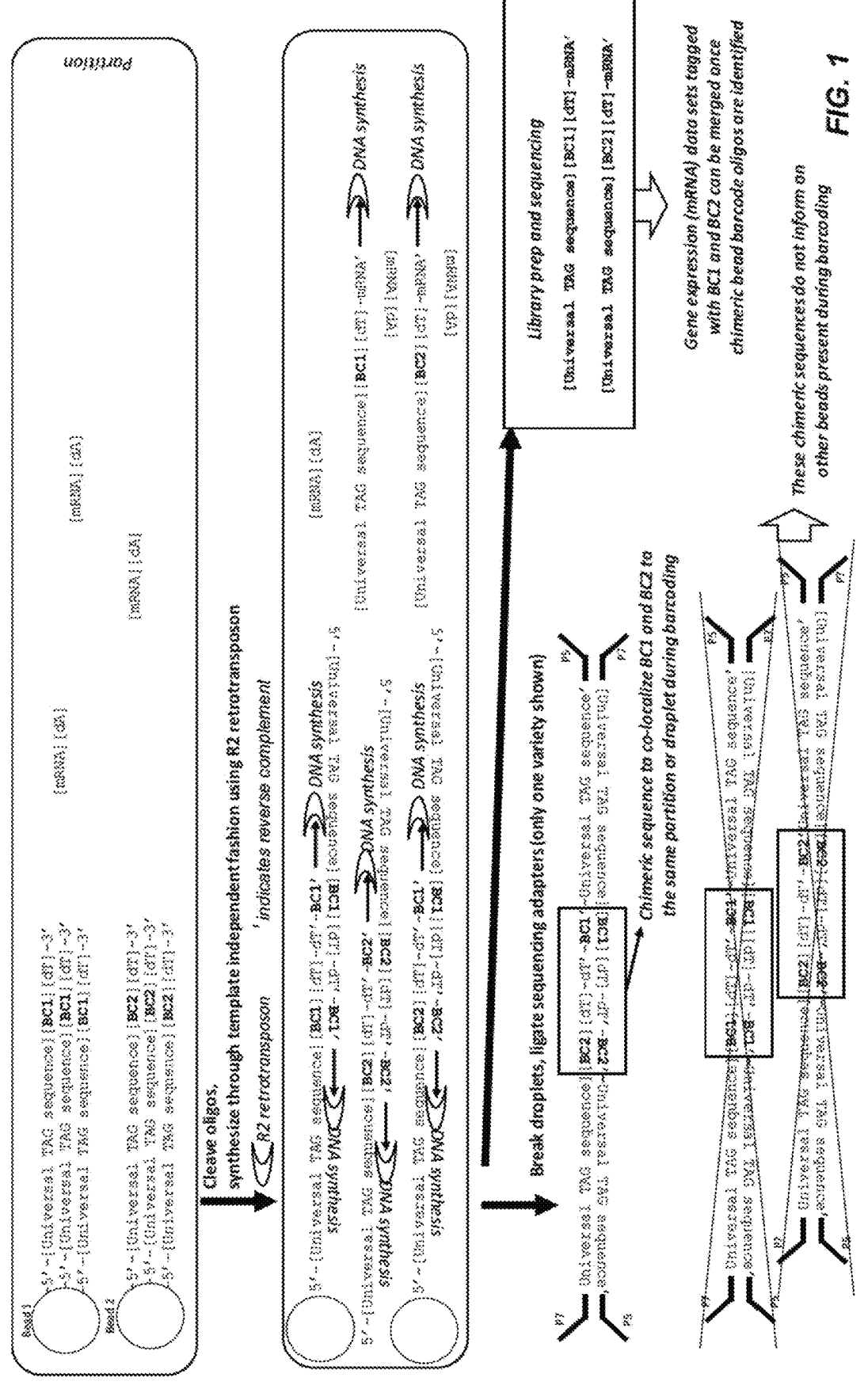
FIG. 1 shows a representative embodiment of template independent barcode oligo joining. During partitioning, more than one barcode bead are encapsulated in single partitions. The oligos are cleaved so that they are no longer physically associated with the bead. R2 retrotransposon finds the 3' end of the barcode oligo and initiates synthesis from the 3' end of a second barcode oligo sequence. These fragments are then adapted, for example through ligation as shown here, and sequenced. The observation of multiple barcode sequences in a single stretch of sequence indicates that the barcode beads were present in the same partition during barcoding. The universal TAG sequence can be used in downstream PCR or during sequencing. Ligation based library prep is indicated.

Unless defined otherwise, all technical and scientific terms used herein generally have the same meaning as commonly understood by one of ordinary skill in the art to which this disclosure belongs. Generally, the nomenclature used herein and the laboratory procedures in cell culture, molecular genetics, organic chemistry, and nucleic acid chemistry and hybridization described below are those well-known and commonly employed in the art. Standard techniques are used for nucleic acid and peptide synthesis. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document. The nomenclature used herein and the laboratory procedures in analytical chemistry, and organic synthetic described below are those well-known and commonly employed in the art.

The term "amplification reaction" refers to any in vitro means for multiplying the copies of a target sequence of nucleic acid in a linear or exponential manner. Such methods include but are not limited to polymerase chain reaction (PCR); DNA ligase chain reaction (see U.S. Pat. Nos. 4,683,195 and 4,683,202; PCR Protocols: A Guide to Methods and Applications (Innis et al., eds, 1990)) (LCR); QBeta RNA replicase and RNA transcription-based amplification reactions (e.g., amplification that involves T7, T3, or SP6 primed RNA polymerization), such as the transcription amplification system (TAS), nucleic acid sequence based amplification (NASBA), and self-sustained sequence replication (3SR); isothermal amplification reactions (e.g., single-primer isothermal amplification (SPIA)); as well as others known to those of skill in the art.

"Amplifying" refers to a step of submitting a solution to conditions sufficient to allow for amplification of a polynucleotide if all of the components of the reaction are intact. Components of an amplification reaction include, e.g., primers, a polynucleotide template, polymerase, nucleotides, and the like. The term "amplifying" typically refers to an "exponential" increase in target nucleic acid. However, "amplifying" as used herein can also refer to linear increases in the numbers of a select target sequence of nucleic acid, such as is obtained with cycle sequencing or linear amplification. In an exemplary embodiment, amplifying refers to PCR amplification using a first and a second amplification primer.

The term "amplification reaction mixture" refers to an aqueous solution comprising the various reagents used to amplify a target nucleic acid. These include enzymes, aqueous buffers, salts, amplification primers, target nucleic acid, and nucleoside triphosphates. Amplification reaction mixtures may also further include stabilizers and other additives to optimize efficiency and specificity. Depending upon the context, the mixture can be either a complete or incomplete amplification reaction mixture "Polymerase chain reaction" or "PCR" refers to a method whereby a specific segment or subsequence of a target double-stranded DNA, is amplified in a geometric progression. PCR is well known to those of skill in the art; see, e.g., U.S. Pat. Nos. 4,683,195 and 4,683,202; and PCR Protocols: A Guide to Methods and Applications, Innis et al., eds, 1990. Exemplary PCR reaction conditions typically comprise either two or three step cycles. Two step cycles have a denaturation step followed by a hybridization/elongation step. Three step cycles comprise a denaturation step followed by a hybridization step followed by a separate elongation step.

A "primer" refers to a polynucleotide sequence that hybridizes to a sequence on a target nucleic acid and serves as a point of initiation of nucleic acid synthesis. Primers can be of a variety of lengths and are often less than 50 nucleotides in length, for example 12-30 nucleotides, in length. The length and sequences of primers for use in PCR can be designed based on principles known to those of skill in the art, see, e.g., Innis et al., supra. Primers can be DNA, RNA, or a chimera of DNA and RNA portions. In some cases, primers can include one or more modified or non-natural nucleotide bases. In some cases, primers are labeled.

A nucleic acid, or a portion thereof, "hybridizes" to another nucleic acid under conditions such that non-specific hybridization is minimal at a defined temperature in a physiological buffer (e.g., pH 6-9, 25-150 mM chloride salt). In some cases, a nucleic acid, or portion thereof, hybridizes to a conserved sequence shared among a group of target nucleic acids. In some cases, a primer, or portion thereof, can hybridize to a primer binding site if there are at least about 6, 8, 10, 12, 14, 16, or 18 contiguous complementary nucleotides, including "universal" nucleotides that are complementary to more than one nucleotide partner. Alternatively, a primer, or portion thereof, can hybridize to a primer binding site if there are fewer than 1 or 2 complementarity mismatches over at least about 12, 14, 16, or 18 contiguous complementary nucleotides. In some embodiments, the defined temperature at which specific hybridization occurs is room temperature. In some embodiments, the defined temperature at which specific hybridization occurs is higher than room temperature. In some embodiments, the defined temperature at which specific hybridization occurs is at least about 37, 40, 42, 45, 50, 55, 60, 65, 70, 75, or 80° C. In some embodiments, the defined temperature at which specific hybridization occurs is 37, 40, 42, 45, 50, 55, 60, 65, 70, 75, or 80° C.

A "template" refers to a polynucleotide sequence that comprises the polynucleotide to be amplified, flanked by or a pair of primer hybridization sites. Thus, a "target template" comprises the target polynucleotide sequence adjacent to at least one hybridization site for a primer. In some cases, a "target template" comprises the target polynucleotide sequence flanked by a hybridization site for a "forward" primer and a "reverse" primer.

As used herein, "nucleic acid" means DNA, RNA, single-stranded, double-stranded, or more highly aggregated hybridization motifs, and any chemical modifications thereof.

Modifications include, but are not limited to, those providing chemical groups that incorporate additional charge, polarizability, hydrogen bonding, electrostatic interaction, points of attachment and functionality to the nucleic acid ligand bases or to the nucleic acid ligand as a whole. Such modifications include, but are not limited to, peptide nucleic acids (PNAs), phosphodiester group modifications (e.g., phosphorothioates, methylphosphonates), 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases, isocytidine and isoguanidine and the like. Nucleic acids can also include non-natural bases, such as, for example, nitroindole. Modifications can also include 3' and 5' modifications including but not limited to capping with a fluorophore (e.g., quantum dot) or another moiety.

A "polymerase" refers to an enzyme that performs template-directed synthesis of polynucleotides, e.g., DNA and/or RNA. The term encompasses both the full length polypeptide and a domain that has polymerase activity. DNA polymerases are well-known to those skilled in the art, including but not limited to DNA polymerases isolated or derived from *Pyrococcus furiosus, Thermococcus litoralis*, and *Thermotoga* maritime, or modified versions thereof. Additional examples of commercially available polymerase enzymes include, but are not limited to: Klenow fragment (New England Biolabs® Inc.), Taq DNA polymerase (QIAGEN), 9° N™ DNA polymerase (New England Biolabs® Inc.), Deep Vent™ DNA polymerase (New England Biolabs® Inc.), Manta DNA polymerase (Enzymatics®), Bst DNA polymerase (New England Biolabs® Inc.), and phi29 DNA polymerase (New England Biolabs® Inc.).

Polymerases include both DNA-dependent polymerases and RNA-dependent polymerases such as reverse transcriptase. At least five families of DNA-dependent DNA polymerases are known, although most fall into families A, B and C. Other types of DNA polymerases include phage polymerases. Similarly, RNA polymerases typically include eukaryotic RNA polymerases I, II, and III, and bacterial RNA polymerases as well as phage and viral polymerases. RNA polymerases can be DNA-dependent and RNA-dependent.

As used herein, the term "partitioning" or "partitioned" refers to separating a sample into a plurality of portions, or "partitions." Partitions are generally physical, such that a sample in one partition does not, or does not substantially, mix with a sample in an adjacent partition. Partitions can be solid or fluid. In some embodiments, a partition is a solid partition, e.g., a microchannel. In some embodiments, a partition is a fluid partition, e.g., a droplet. In some embodiments, a fluid partition (e.g., a droplet) is a mixture of immiscible fluids (e.g., water and oil). In some embodiments, a fluid partition (e.g., a droplet) is an aqueous droplet that is surrounded by an immiscible carrier fluid (e.g., oil).

As used herein a "barcode" is a short nucleotide sequence (e.g., at least about 4, 6, 8, 10, or 12, nucleotides long) that identifies a molecule to which it is conjugated. Barcodes can be used, e.g., to identify molecules in a partition. Such a partition-specific barcode should be unique for that partition as compared to barcodes present in other partitions. For example, partitions containing target RNA from single-cells can subject to reverse transcription conditions using primers that contain a different partition-specific barcode sequence in each partition, thus incorporating a copy of a unique "cellular barcode" into the reverse transcribed nucleic acids of each partition. Thus, nucleic acid from each cell can be distinguished from nucleic acid of other cells due to the unique "cellular barcode." In some cases, the cellular barcode is provided by a "particle barcode" that is present on oligonucleotides conjugated to a particle, wherein the particle barcode is shared by (e.g., identical or substantially identical amongst) all, or substantially all, of the oligonucleotides conjugated to that particle. Thus, cellular and particle barcodes can be present in a partition, attached to a particle, or bound to cellular nucleic acid as multiple copies of the same barcode sequence. Cellular or particle barcodes of the same sequence can be identified as deriving from the same cell, partition, or particle. Such partition-specific, cellular, or particle barcodes can be generated using a variety of methods, which methods result in the barcode conjugated to or incorporated into a solid or hydrogel support (e.g., a solid bead or particle or hydrogel bead or particle). In some cases, the partition-specific, cellular, or particle barcode is generated using a split and mix (also referred to as split and pool) synthetic scheme as described herein. A partition-specific barcode can be a cellular barcode and/or a particle barcode. Similarly, a cellular barcode can be a partition specific barcode and/or a particle barcode. Additionally, a particle barcode can be a cellular barcode and/or a partition-specific barcode.

In other cases, barcodes uniquely identify the molecule to which it is conjugated. For example, by performing reverse transcription using primers that each contain a unique "molecular barcode." In still other examples, primers can be utilized that contain "partition-specific barcodes" unique to each partition, and "molecular barcodes" unique to each molecule. After barcoding, partitions can then be combined, and optionally amplified, while maintaining virtual partitioning. Thus, e.g., the presence or absence of a target nucleic acid (e.g., reverse transcribed nucleic acid) comprising each barcode can be counted (e.g. by sequencing) without the necessity of maintaining physical partitions.

The length of the barcode sequence determines how many unique samples can be differentiated. For example, a 1 nucleotide barcode can differentiate 4, or fewer, different samples or molecules; a 4 nucleotide barcode can differentiate $4^4$ or 256 samples or less; a 6 nucleotide barcode can differentiate 4096 different samples or less; and an 8 nucleotide barcode can index 65,536 different samples or less. Additionally, barcodes can be attached to both strands either through barcoded primers for both first and second strand synthesis, through ligation, or in a tagmentation reaction.

Barcodes are typically synthesized and/or polymerized (e.g., amplified) using processes that are inherently inexact. Thus, barcodes that are meant to be uniform (e.g., a cellular, particle, or partition-specific barcode shared amongst all barcoded nucleic acid of a single partition, cell, or bead) can contain various N-1 deletions or other mutations from the canonical barcode sequence. Thus, barcodes that are referred to as "identical" or "substantially identical" copies refer to barcodes that differ due to one or more errors in, e.g., synthesis, polymerization, or purification errors, and thus contain various N-1 deletions or other mutations from the canonical barcode sequence. Moreover, the random conjugation of barcode nucleotides during synthesis using e.g., a split and pool approach and/or an equal mixture of nucleotide precursor molecules as described herein, can lead to low probability events in which a barcode is not absolutely unique (e.g., different from all other barcodes of a population or different from barcodes of a different partition, cell, or bead). However, such minor variations from theoretically ideal barcodes do not interfere with the high-throughput sequencing analysis methods, compositions, and kits described herein. Therefore, as used herein, the term "unique" in the context of a particle, cellular, partition-specific, or molecular barcode encompasses various inadvertent N-1 deletions and mutations from the ideal barcode sequence. In some cases, issues due to the inexact nature of barcode synthesis, polymerization, and/or amplification, are overcome by oversampling of possible barcode sequences as compared to the number of barcode sequences to be distinguished (e.g., at least about 2-, 5-, 10-fold or more possible barcode sequences). For example, 10,000 cells can be analyzed using a cellular barcode having 9 barcode nucleotides, representing 262,144 possible barcode sequences. The use of barcode technology is well known in the art, see for example Katsuyuki Shiroguchi, et al. Proc Natl Acad Sci USA., 2012 Jan 24; 109(4):1347-52; and Smith, A M et al., Nucleic Acids Research Can 11, (2010). Further methods and compositions for using barcode technology include those described in U.S. 2016/0060621.

A "transposase" or "tagmentase" means an enzyme that is capable of forming a functional complex with a transposon end-containing composition and catalyzing insertion or transposition of the transposon end-containing composition into the double-stranded target DNA with which it is incubated in an in vitro transposition reaction.

The term "transposon end" means a double-stranded DNA that exhibits only the nucleotide sequences (the "transposon end sequences") that are necessary to form the complex with the transposase that is functional in an in vitro transposition reaction. A transposon end forms a "complex" or a "synaptic complex" or a "transposome complex" or a "transposome composition with a transposase or integrase that recognizes and binds to the transposon end, and which complex is capable of inserting or transposing the transposon end into target DNA with which it is incubated in an in vitro transposition reaction. A transposon end exhibits two complementary sequences consisting of a "transferred transposon end sequence" or "transferred strand" and a "non-transferred transposon end sequence," or "non transferred strand" For example, one transposon end that forms a complex with a hyperactive Tn5 transposase (e.g., EZ-Tn5™ Transposase, EPICENTRE Biotechnologies, Madison, Wis., USA) that is active in an in vitro transposition reaction comprises a transferred strand that exhibits a "transferred transposon end sequence" as follows:

(SEQ ID NO: 1)

5' AGATGTGTATAAGAGACAG 3', and a non-transferred strand that exhibits a "non-transferred transposon end sequence" as follows:

(SEQ ID NO: 2)

5' CTGTCTCTTATACACATCT 3'.

The 3'-end of a transferred strand is joined or transferred to target DNA in an in vitro transposition reaction. The non-transferred strand, which exhibits a transposon end sequence that is complementary to the transferred transposon end sequence, is not joined or transferred to the target DNA in an in vitro transposition reaction.

In some embodiments, the transferred strand and non-transferred strand are covalently joined. For example, in some embodiments, the transferred and non-transferred strand sequences are provided on a single oligonucleotide, e.g., in a hairpin configuration. As such, although the free end of the non-transferred strand is not joined to the target DNA directly by the transposition reaction, the non-transferred strand becomes attached to the DNA fragment indirectly, because the non-transferred strand is linked to the transferred strand by the loop of the hairpin structure.

The term "solid support" refers to the surface of a bead, microtiter well or other surface that is useful for attaching a nucleic acid, such as an oligonucleotide or polynucleotide. The surface of the solid support can be treated to facilitate attachment of a nucleic acid, such as a single stranded nucleic acid.

The term "bead" refers to any solid support that can be in a partition, e.g., a small particle or other solid support. In some embodiments, the beads comprise polyacrylamide. For example, in some embodiments, the beads incorporate barcode oligonucleotides into the gel matrix through an acrydite chemical modification attached to each oligonucleotide. Exemplary beads can include hydrogel beads. In some cases, the hydrogel is in sol form. In some cases, the hydrogel is in gel form. An exemplary hydrogel is an agarose hydrogel. Other hydrogels include, but are not limited to, those described in, e.g., U.S. Pat. Nos. 4,438,258; 6,534,083; 8,008,476; 8,329,763; U.S. Patent Appl. Nos. 2002/0,009, 591; 2013/0,022,569; 2013/0,034,592; and International Patent Publication Nos. WO/1997/030092; and WO/2001/049240.

The term "capture sequence" refers to a nucleic acid sequence complementary to the 3' sequence, or a reverse complement thereof, of another sequence, such as a detector sequence or sample target sequence.

The term "detector sequence" refers to a sequence at the 3' end of oligonucleotides that are complementary to the capture sequence. The detector sequence is either covalently or non-covalently associated with other sequences that are unique to the linked detector sequence. The other sequences that are unique may comprise molecular barcodes, nucleotide sequence barcodes, and/or nucleotide length barcodes. The nucleic acids that contain the detector sequence may have cleavable moieties.

It will be understood that any range of numerical values disclosed herein can include the endpoints of the range, and any values or subranges in between the endpoints. For example, the range 1 to 10 includes the endpoints 1 and 10, and any value between 1 and 10. The values typically include one significant digit.

The term "sample" refers to a biological composition, such as a cell, comprising a target nucleic acid.

The term "deconvolution" refers to the assignment of 2 barcodes and the beads they were attached to as being from the same partition or originally occupying the same partition. Deconvolution can be determined by the detection of the two barcodes on a single nucleic acid fragment during sequencing.

The term "about" refers to the usual error range for the respective value that is known by a person of ordinary skill in the art for this technical field, for example, a range of ±10%, ±5%, or ±10% can encompass the recited value, even if the recited value is not modified by the term "about."

All ranges described herein can include the end point values of the range, and any sub-range of values included between the endpoints of the range, where the values include the first significant digit. For example, a range of 1 to 10 includes a range from 2 to 9, 3 to 8, 4 to 7, 5 to 6, 1 to 5, 2 to 5, 2 to 10, 3 to 10, and so on.

DETAILED DESCRIPTION OF THE INVENTION

Barcode bead overloading in partitions such as droplets increases droplet utilization, such that >90% of droplets contain at least one solid support (such as a bead) and are active during barcoding. However, to prevent the fractionation of the substrate (i.e., cell) data, and/or the over representation of the substrate (i.e., cell) when a partition has more than one solid support, solid supports need to be co-localized to single partitions. When this occurs, the data for each of the co-localized barcodes can be merged in silico to preserve data integrity.

The problems associated with more than one barcoded bead per partition can be solved by the methods and compositions described herein. For example, co-localizing and attributing those barcodes to their original shared partitions through molecular biology sequence analysis can ensure data integrity, and, in consequence, enable bead overloading into partitions as a method to maximize the barcoding conversion rates of the partitions. The instant disclosure provides compositions, methods, synthesized sequence structures and sequence analysis that can be used to co-localize barcodes to their shared partitions where barcoding occurred.

Specifically, sequencing the barcode sequences in a single linear stretch of DNA, enables the inference that the beads from which these oligos originated were located in the same partition during the barcoding reaction. Upon co-localization of the barcode oligos, the data attributed to each barcode can be merged in silico to create a unified partition level barcode and an intact data set for the substrates that were originally contained within the partition, i.e., coming from a single cell.

The formation of barcode-barcode linear sequence structures can be achieved through a variety of methods, some of which are primer template dependent or independent, using RNA dependent polymerases (e.g., reverse transcriptases), DNA dependent polymerases, ligases (RNA, DNA, single or double stranded) or R2 retrotransposon. The physical association of barcode oligos typically occurs in the partition. The enzymology covalently linking the sequences either by synthesis of physically bound, e.g, hybridized, template, or by direct linking can occur either inside or outside of the partitions or droplets. The association of the barcode oligos can be facilitated by specific sequences, such as palindromes.

Described herein are oligonucleotides that can be attached to solid supports. In some embodiments, the oligonucleotides comprise a barcode sequence that is unique for the solid support (referred to as a solid support oligonucleotide). In some embodiments, two different solid support oligonucleotides comprising different barcode sequences are joined or linked together to create a chimeric oligonucleotide comprising two different barcode sequences. The two different oligonucleotides comprising different barcode sequences can be attached to different solid supports in the same partition. Following cleavage of the oligonucleotides from the solid supports, the different oligonucleotides are covalently linked to create the chimeric oligonucleotide comprising two different barcode sequences.

The chimeric oligonucleotides can then be sequenced and debarcoded, resulting in the association of barcode sequences in a single linear stretch of DNA, which suggests that the solid supports from which the oligos originated were located in the same partition during the barcoding reaction. Upon co-localization of the barcode oligos, the data attributed to each barcode can be merged in silico to create a unified partition level barcode and an intact data set for the substrates that were originally contained within the partition, i.e., originating from a single cell.

The formation of barcode oligo chimeras can be achieved through a variety of methods, including primer template dependent or template independent methods, such as RNA dependent polymerases, e.g., reverse transcriptases, DNA dependent polymerases, ligases (RNA, DNA, single or double stranded) or R2 retrotransposon. In some embodiments, the physical association of barcode oligos occurs inside the partition. In some embodiments, the reactions covalently linking the sequences, either by synthesis of physically bound, i.e., hybridized, template, or by direct linking can occur either inside or outside of the partitions or droplets. The association of the barcode oligos can be facilitated by specific sequences, such as palindromes.

The inventors have surprisingly and unexpectedly found that template independent enzymatic reactions, such as R2 retrotransposon and reverse transcriptase, can produce chimeric oligonucleotides comprising two different barcodes that were originally attached to different solid supports in the partition.

Methods

Described herein are methods for detecting the presence of multiple barcoded solid supports in partitions. The methods comprise providing a plurality of partitions wherein at least some partitions comprise multiple solid supports. The partition can be a droplet in an emulsion. In some embodiments, each solid support is linked or attached to a different oligonucleotide (a solid support oligonucleotide) than other solid supports in the partition. In some embodiments, the solid support oligonucleotide comprises a barcode unique for the solid support. For example, the oligonucleotide can include a barcode specific for the particular solid support to which it is linked. In some embodiments, a first solid support is attached to a first solid support oligonucleotide comprising a first barcode unique for the first solid support, and a second solid support is attached to a second solid support oligonucleotide comprising a second barcode unique for the second solid support. It will be understood that a solid support can be attached to multiple copies of the same solid support oligonucleotide, for example, at least about 10, 50, 100, 500, 1000, 5000, 10,000, 50,000, 100,000, 500,000, 1,000,000, 5,000,000, 10,000,000, $10^8$, $10^9$, $10^{10}$ or more copies of the same or substantially identical solid support oligonucleotide can be attached to one (e.g., the same) solid support.

In some embodiments, the barcode is a sequence of about 4 to about 250 nucleotides, e.g., about 6-25, about 10-24, about 8-20, about 8-18, about 10-20, about 10-18, or about 12-20 nucleotides. In some embodiments, the barcode is a sequence of at least 4, 6, 8, 10, or 12 nucleotides. In some embodiments, the oligonucleotides conjugated to a particular solid surface (e.g., bead) comprise a barcode sequence that is the same or substantially the same among the plurality of oligonucleotides on the solid surface, but unique or substantially unique as compared to the plurality of oligonucleotides attached to other solid surfaces. In some embodiments, the barcode can be broken into two or more non-contiguous sequences.

In some embodiments, the method comprises synthesizing a complementary sequence of the oligonucleotides to produce a double-stranded polynucleotide having barcodes from two of the solid support oligonucleotides. Thus, the double-stranded polynucleotide can comprise two different barcodes, a first barcode from a first solid support oligonucleotide, and a second barcode from a second solid support oligonucleotide.

In some embodiments, the step of synthesizing a complementary sequence of the oligonucleotides to produce a double-stranded polynucleotide occurs inside the partition (i.e., before the contents of the partitions are released). In some embodiments, the step of synthesizing a complementary sequence of the oligonucleotides to produce a double-stranded polynucleotide occurs outside the partition (i.e., after the contents of the partitions are released). In some cases, the contents of multiple partitions are combined prior to downstream steps, such as sequencing the strands of the double-stranded polynucleotides.

In some embodiments, the method comprises sequencing one or both strands of the double-stranded polynucleotides. The presence of sequences comprising two different barcodes indicates that two solid supports attached to different solid support oligonucleotides were present in the same partition.

In some embodiments, the solid support oligonucleotides comprising barcodes are cleaved from the solid supports, for example, while the oligonucleotides are inside the partition. In some embodiments, the solid support oligonucleotides are linked to the solid support via a cleavable linker (as described below) and can be cleaved from the bead or solid support in the partitions.

In some cases, the solid support oligonucleotide is attached to a solid support through a disulfide linkage (e.g., through a disulfide bond between a sulfide of the solid support and a sulfide covalently attached to the 5' or 3' end, or an intervening nucleic acid, of the oligonucleotide). In such cases, the oligonucleotide can be cleaved from the solid support by contacting the solid support with a reducing agent such as a thiol or phosphine reagent, including but not limited to a beta mercaptoethanol, dithiothreitol (DTT), or tris(2-carboxyethyl)phosphine (TCEP). In some embodiments, the cleavable linker is a restriction enzyme site that is cleaved by a restriction enzyme (e.g., an endonuclease such as a Type II endonuclease or Type IIS endonuclease). For example, in some embodiments, the cleavable linker comprises a Type II restriction enzyme binding site (e.g., HhaI, HindIII, NotI, BbvCI, EcoRI, BglI) or a Type IIS restriction enzyme binding site (e.g., FokI, AlwI, BspMI, MnlI, BbvI, BccI, MboI). In some embodiments, the cleavable linker comprises a uridine incorporated site in a portion of a nucleotide sequence. A uridine incorporated site can be cleaved, for example, using a uracil glycosylase enzyme (e.g., a uracil N-glycosylase enzyme or uracil DNA glycosylase (UDG) enzyme). In some embodiments, the cleavable linker comprises a photocleavable nucleotide. Photocleavable nucleotides include, for example, photocleavable fluorescent nucleotides and photocleavable biotinylated nucleotides. See, e.g., Li et al., *PNAS*, 2003, 100:414-419; Luo et al., *Methods Enzymol*, 2014, 549:115-131.

In some embodiments, the complementary sequence is synthesized using template independent mechanisms. For example, in some embodiments, the complementary sequence is synthesized using a R2 retrotransposon (R2 retrotransposase). In some embodiments, the complementary sequence is synthesized using a reverse transcriptase. Suitable reverse transcriptases include Superscript II (Life Tech), Superscript III (Life Tech), Superscript IV (Life Tech), Maxima RNAse+ (Thermo), Maxima RNAse– (Thermo), and Sensiscript (Qiagen). Generally, reverse transcriptases typically include eukaryotic RNA polymerases I, II, and III, and bacterial RNA polymerases as well as phage and viral polymerases. RNA polymerases can be DNA-dependent and RNA-dependent. RNA polymerases can have RNAse H+ activity and RNAse H– activity.

In some embodiments, the method further comprises adding double stranded adapters to the double-stranded polynucleotide. The double stranded adapters can be added by contacting the double-stranded polynucleotide with an adapter-loaded transposase or tagmentase. Adapter-loaded tagmentases are described herein and in US 2018/0195112 (corresponding to WO 2018/118971).

FIG. 1 illustrates one embodiment of template independent synthesis. Two different beads are shown in the same partition, and each bead is attached to an oligonucleotide comprising a universal tag sequence, a barcode (BC), and a poly dT sequence. The oligonucleotide attached to Bead 1 comprises BC1, and the oligonucleotide attached to Bead 2 comprises a different barcode, BC2. The oligonucleotides are cleaved from the beads, and R2 retrotransposon (present inside the partition as part of the reaction mixture) initiates synthesis from the 3' end of the oligonucleotides and produces a mixture of double stranded DNA molecules. As shown in the lower partition, some of the double stranded molecules in the mixture contain both barcodes BC1 and BC2 (see molecule illustrated at bottom of partition). The emulsion is then broken, releasing the contents of the partitions, and sequencing adapters are added by ligation. The universal TAG sequence can be used in downstream PCR or during sequencing. Ligation based library preparation is shown in the lower right gray box. The presence of the chimeric sequence containing two barcodes in a single sequence read indicates that the two different barcode beads were present in the same partition during barcoding.

Figure 2:
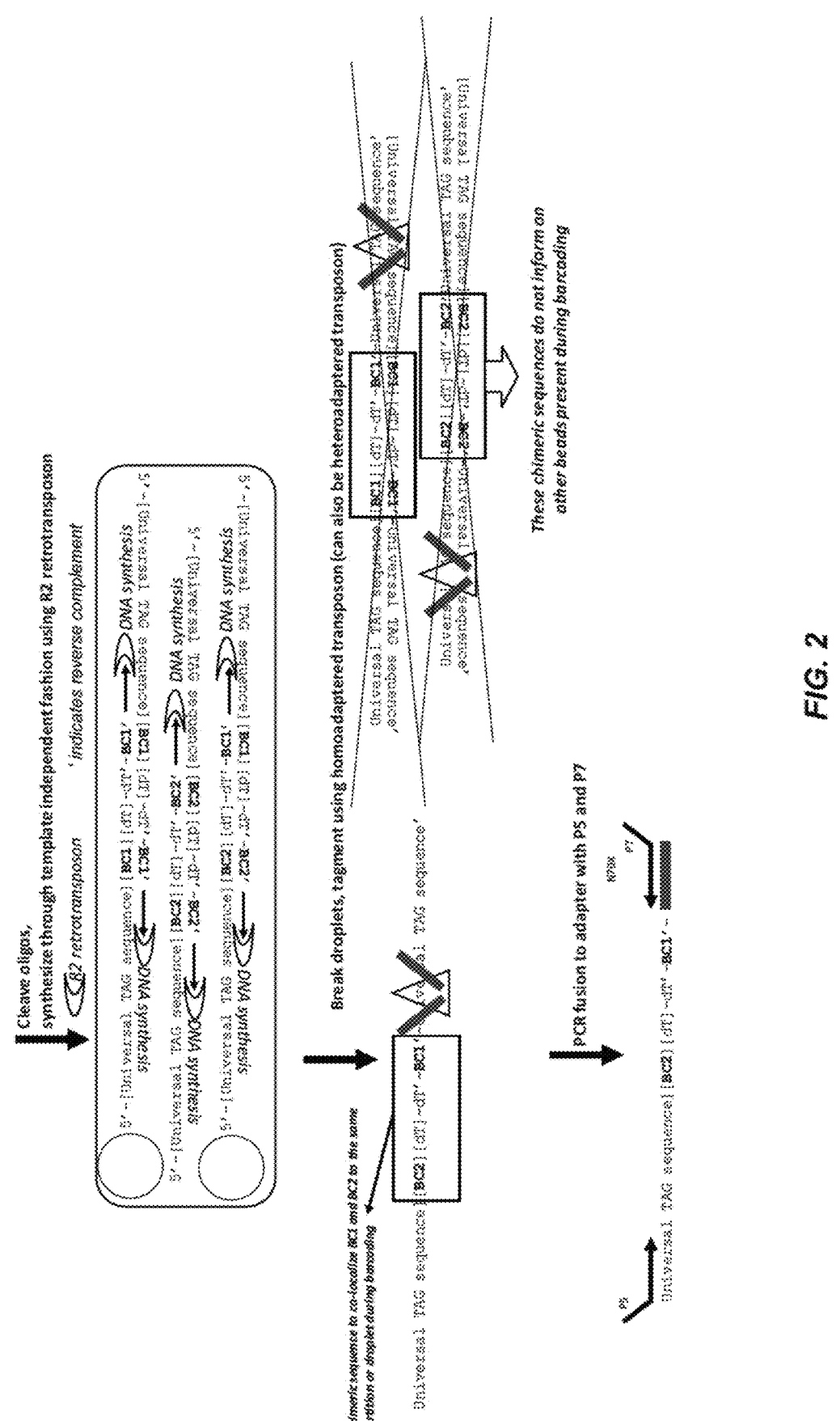
FIG. 2 shows a representative embodiment of transposase based library preparation of chimeric bead oligo sequences. The steps shown in the figure are similar to FIG. 1, except that transposases are used to finalize library preparation. The triangle represents the transposase/tagmentase, and the solid black bars represent adapters.

FIG. 2 illustrates another embodiment of template independent synthesis. The steps are the same as those shown in FIG. 1, except that transposases are used to add adapters for library preparation after the emulsion is broken. The triangle represents the transposase/tagmentase, and the solid black bars represent the adapters.

Figure 3:
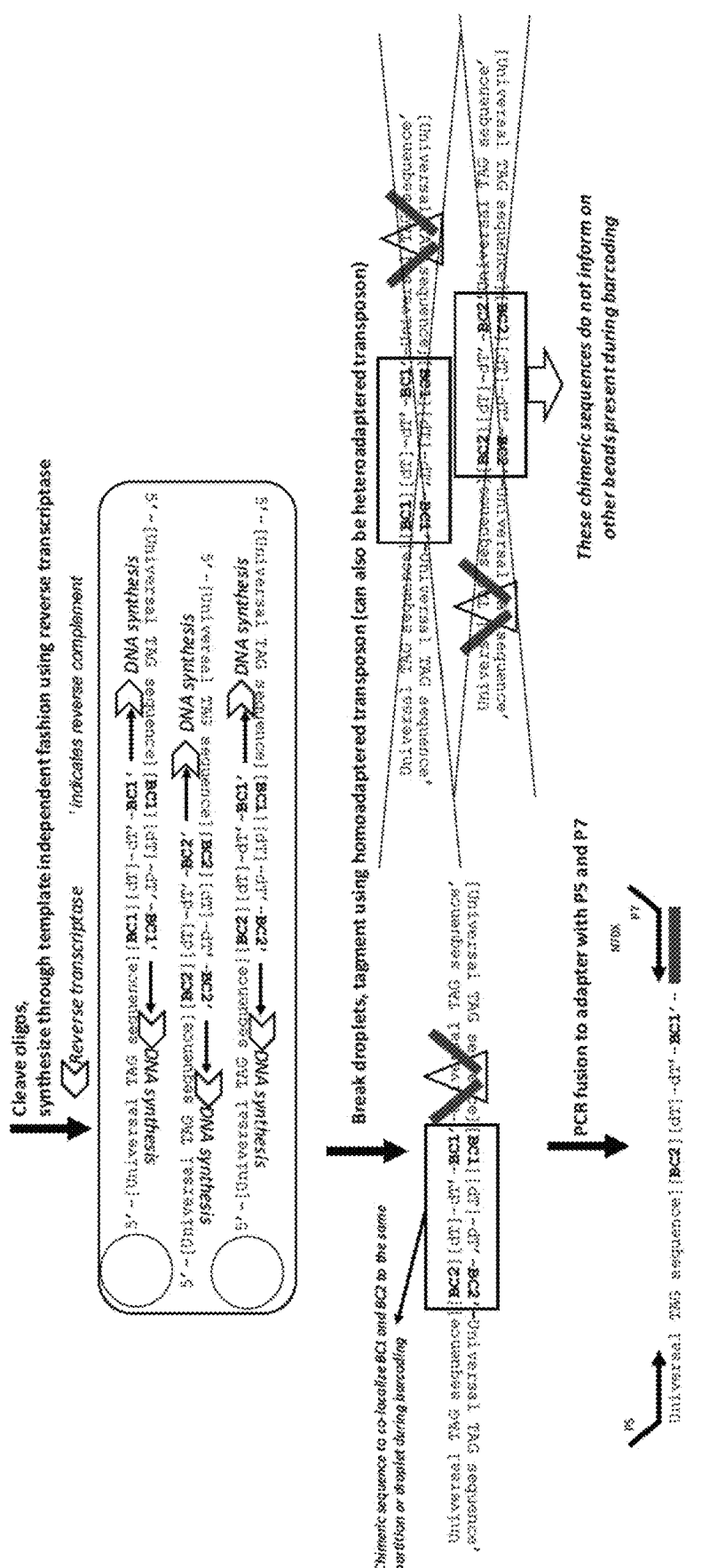
FIG. 3 shows a representative embodiment of reverse transcriptase generation of chimeric bead oligo sequences. The steps shown in the figure are similar to FIG. 2, except that template independent barcode synthesis occurs as a secondary reaction from reverse transcriptases.

FIG. 3 illustrates another embodiment of template independent synthesis. The steps are similar to FIG. 2, except that template independent barcode synthesis occurs as a secondary reaction from reverse transcriptase generation of chimeric bead oligo sequences. As above, some of the double stranded molecules in the partition contain both barcodes BC1 and BC2 (see molecule illustrated at bottom of partition). The presence of the chimeric sequence containing two barcodes in a single sequence read indicates that the two different barcode beads were present in the same partition during barcoding.

FIG. 4 shows a representative example of sequence generated from reverse transcriptase synthesis of chimeric bead oligo sequences, as shown in FIG. 3. Bead oligo barcodes are generated from the combination of barcode (BC) 1, BC2, and BC3. Two different bead barcode oligo sequences are found in read 1 and read 2, respectively. This information from the same read or cluster in an Illumina flow cell co-localizes the relevant beads underlying the barcode sequences to the same partition during the barcode reaction.

Figure 5:
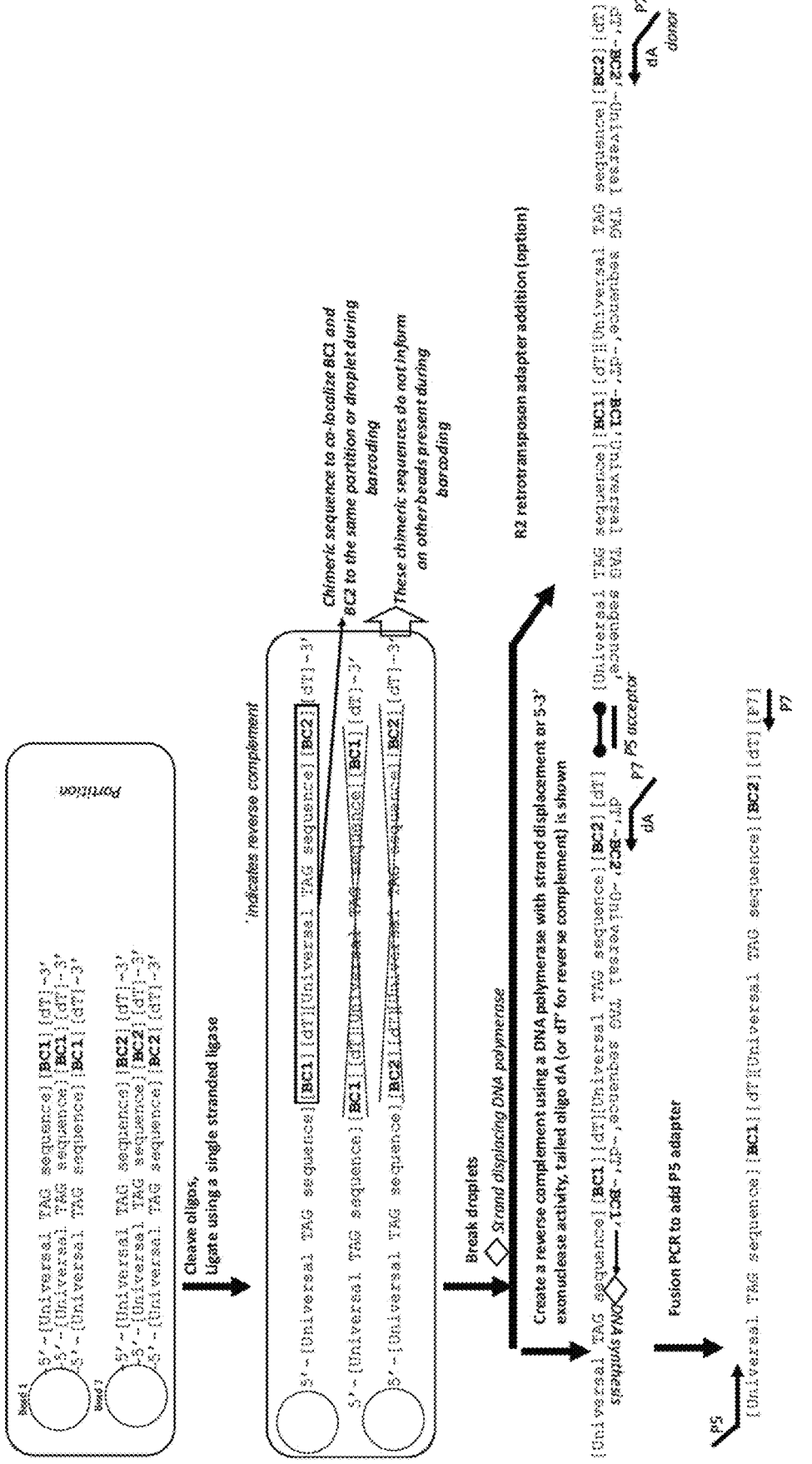
FIG. 5 shows a representative embodiment of direct ligation of bead oligo sequences. During partitioning, more than one barcode bead are encapsulated in single partitions. The oligos are cleaved so that they are no longer physically associated with the bead. Single stranded DNA ligase ligates the barcode bead oligos as shown. The emulsion is broken. The chimers or concatemers are converted into a double stranded product outside of droplets using a P7 tailed poly A primer. The double stranded molecules are prepared for sequencing. Fusion PCR, to add P5 and P7 tags, sample prep is shown; however, this could occur through other methods of library preparation. In an alternative embodiment, 2D retrotransposon is used to adapter the molecules in a single step (shown on the right side).

FIG. 5 illustrates another embodiment of template independent synthesis using ligation to attach the cleaved oligonucleotides. As above, during partitioning more than one barcode bead is encapsulated in single partitions. The oligonucleotides are cleaved so that they are no longer physically associated with the bead. Single stranded DNA ligase randomly ligates the barcode bead oligonucleotides as shown. The emulsion is then broken, and the chimeric molecules or concatemers are converted into a double stranded molecule outside of the partition using a P7 tailed poly A primer. The double stranded molecules are prepared for sequencing, for example, by fusion PCR, to add P5 and P7 tags. Other methods for preparing the double stranded molecules for sequencing are known in the art. For example, in an alternative embodiment, 2D retrotransposon is used to add adapter molecules in a single step (shown on the right side).

Figure 6:
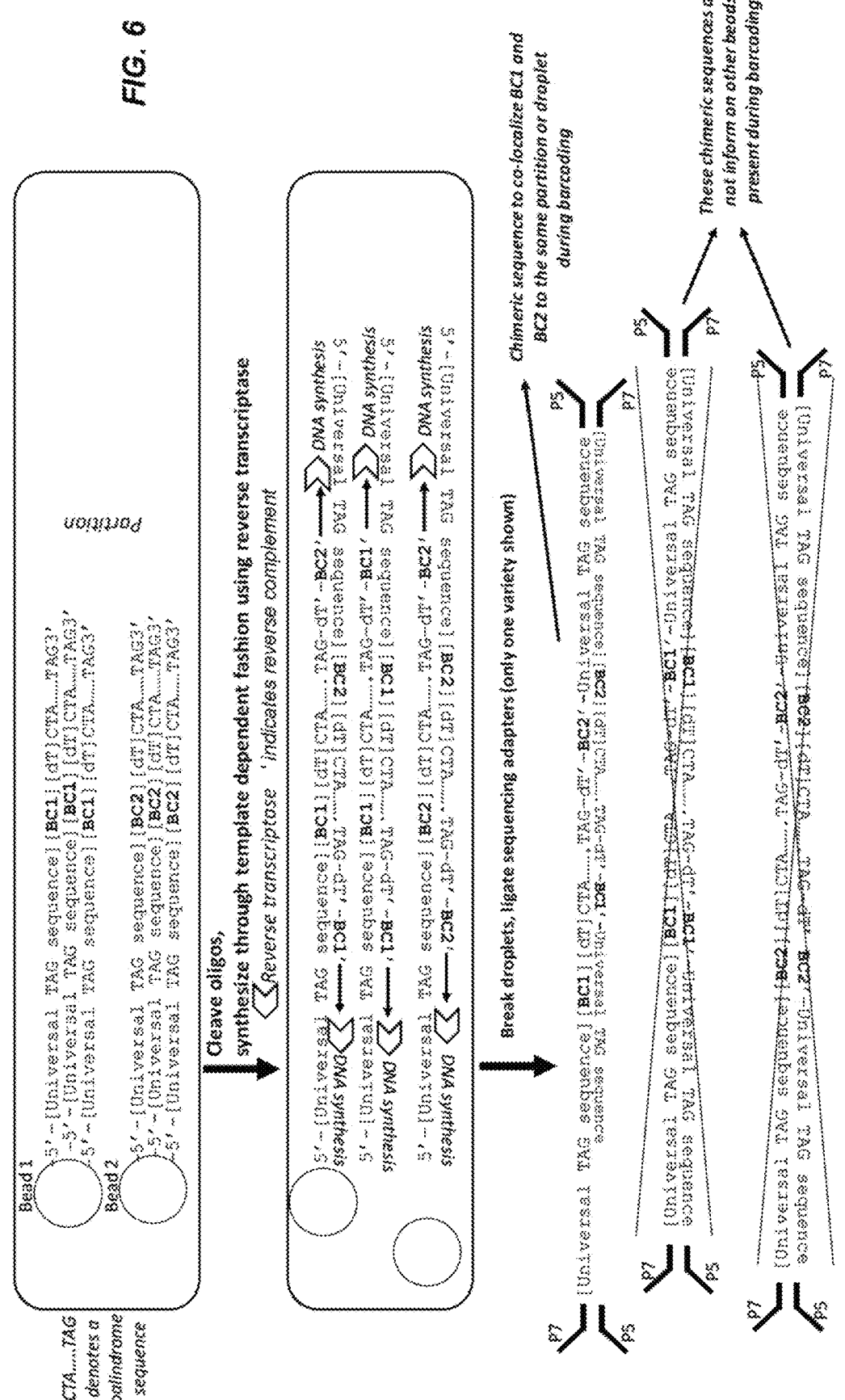
FIG. 6 shows a representative embodiment of template dependent chimer generation in partitions. In this embodiment, the bead oligo sequences have palindromic 3' termini. Oligos are cleaved in the partitions, and a proportion of them hybridize to each other. Reverse transcription synthesizes the reverse complement. Adaptering during library prep is accomplished through fusion PCR, ligation (shown) or other known methods.

FIG. 6 illustrates an embodiment of template dependent chimeric oligonucleotide generation in partitions. In this embodiment, the bead oligonucleotide sequences have palindromic 3' termini. As above, the oligonucleotides are cleaved in the partitions, and a proportion of them hybridize to each other. Reverse transcription is used to synthesize the reverse complement. In this embodiment, sequencing adapters are added by ligation and fusion PCR to prepare the library for sequencing.

A 1:1 ratio of mouse NIH3T3 and human HEK cell lines were mixed and processed through the single cell RNA seq workflow. They were loaded such that an expected 10K cells were expected to be processed.

Upon encapsulation, cells were lysed with standard non ionic detergents and the mRNA reverse transcribed using a MMLV based reverse transcriptase. Reverse transcription was driven through a bead barcode oligo dT primer templated reaction. The cDNA was converted into double stranded cDNA in droplets. The droplets were broken, the contents combined and the products purified using Ampure beads.

After double strand generation, tagmentase was applied to the reaction to tagment the ds-cDNA. A homoadaptered Tn5 tagmentase was used during the tagmentation reaction. The tagmented ds cDNA was then subjected to PCR enrichment of the bead adapted 3' end of the library by using primers specific to the bead oligo universal TAG sequence found on the 5' end of the oligo and the non-Mosaic End portion of the Tn5 adapter, ie using P5 and N70X primers, respectively. Due to PCR suppression, inserts that are adapted by Tn5 adapters only amplify with relatively poor efficiency. The product are purified with Ampure beads and run on a BioAnalyzer gel. The traces for the products are shown in the figure.

In another aspect, the methods use solid supports that are functionalized by attaching solid support oligonucleotides via a linker comprising a uracil base and a biotin-conjugated base. The linker can be located at the 5' end of the detector oligonucleotides. In some embodiments, the oligonucleotide comprises a barcode unique to the solid support. In some embodiments, the oligonucleotide further comprises a sequencing adapter. In some embodiments, the oligonucleotide further comprises a "capture sequence" at the 3' end.

Figure 8:
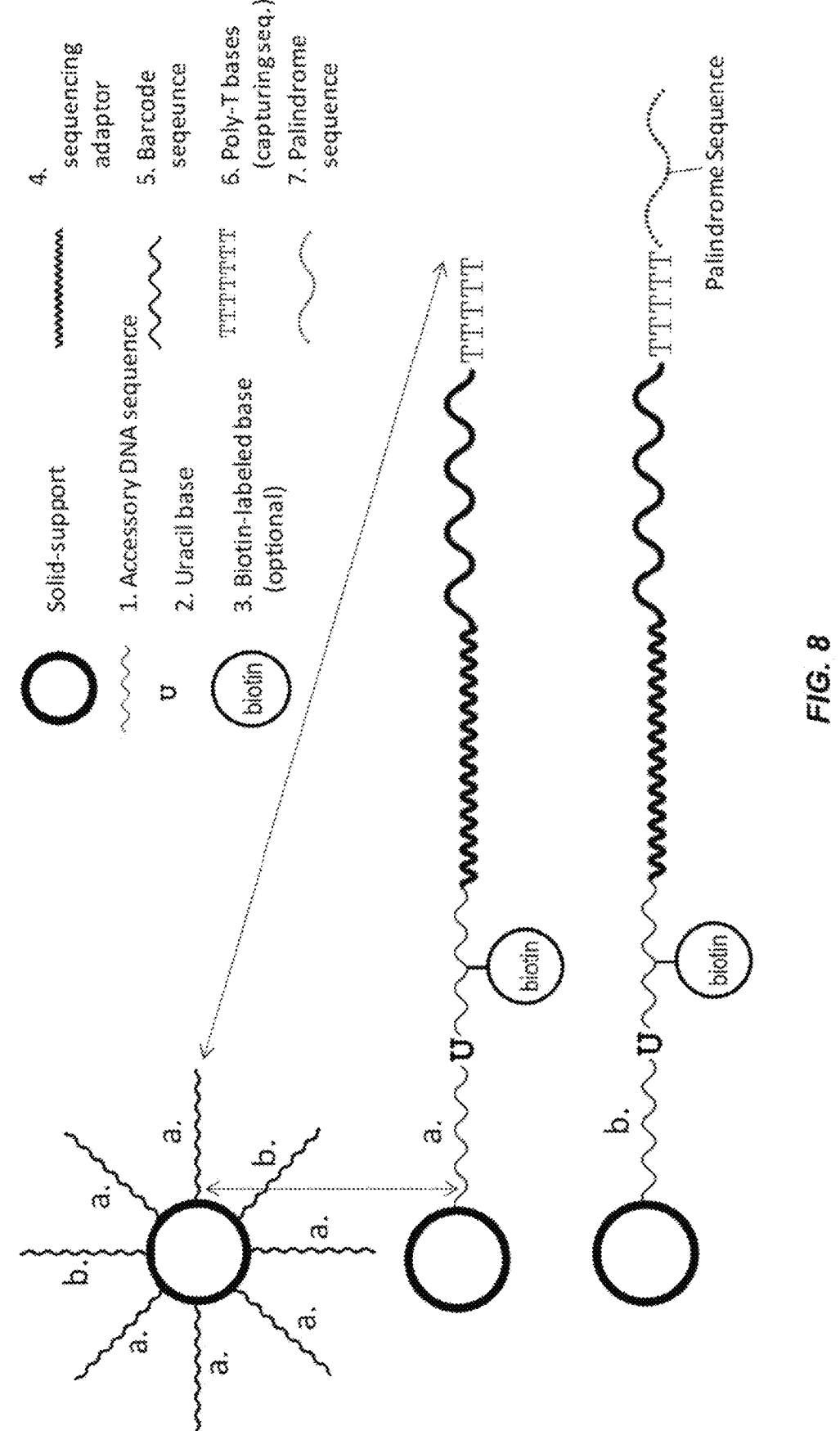
FIG. 8 shows a schematic diagram of the structure of a barcode-oligo conjugated bead (barcode-bead) according to one embodiment described herein. The barcode-bead comprises a solid support (e.g., a bead) and the cargo (barcode-oligos). Each bead carries, at least, two kinds of barcode-oligos, for example "a" and "b", at a ratio of 10,000:1 or above. Barcode-oligo a. comprises (1) an accessory DNA sequence, (2) one or more uracil-base(s), (3) an optional biotin-labeled nucleotide base, (4) a sequencing adaptor sequence, (5) a barcode, and (6) a capturing sequence. Barcode-oligo b. further comprises (7) a palindrome sequence at its 3' end for joining the barcodes. The capture sequence is optional in barcode-oligo b.

In some embodiments, the capture sequence is a 3' poly dT sequence. In some embodiments, the capture sequence is a random sequence. In some embodiments, the capture sequence is a gene-specific sequence. A representative example is shown in FIG. 8.

The beads can be prepared by hybridizing a template (sometimes referred to as a "dummy template" or "detector oligonucleotide") to the solid support oligonucleotide, where the dummy template has a 3' end that is complementary to the capture sequence. For example, in some embodiments, the dummy template comprises a 3' poly A tail that can hybridize to the poly dT capture sequence of the solid support oligonucleotide. The dummy template can comprise a palindromic sequence at the 5' end. In some embodiments, palindromic sequence is 4-250 nucleotides in length, for example, 4-80, 10-20, 10-30, 10-40, 20-30, or 20-40 nucleotides in length. It will be understood that the palindromic sequence comprises a first 5' region and a second 3' region, where at least a portion of the 3' region comprises the reverse complement of the 5' region, such that the first region can be, for example 10 to 20 nucleotides, and the second region can be 10 to 20 nucleotides. In some embodiments, the ratio of solid support oligonucleotides to detector oligonucleotides is at least 5:1 to 100000:1, for example 5:1, 10:1, 100:1, 1000:1, 5000:1, 10000:1, 20000:1; 30000:1. 40000:1, 50000:1; 60000:1, 70000:1; 80000:1, 90000:1 or 100000:1. In some embodiments, the hybridization occurs inside the partition.

Figure 9:
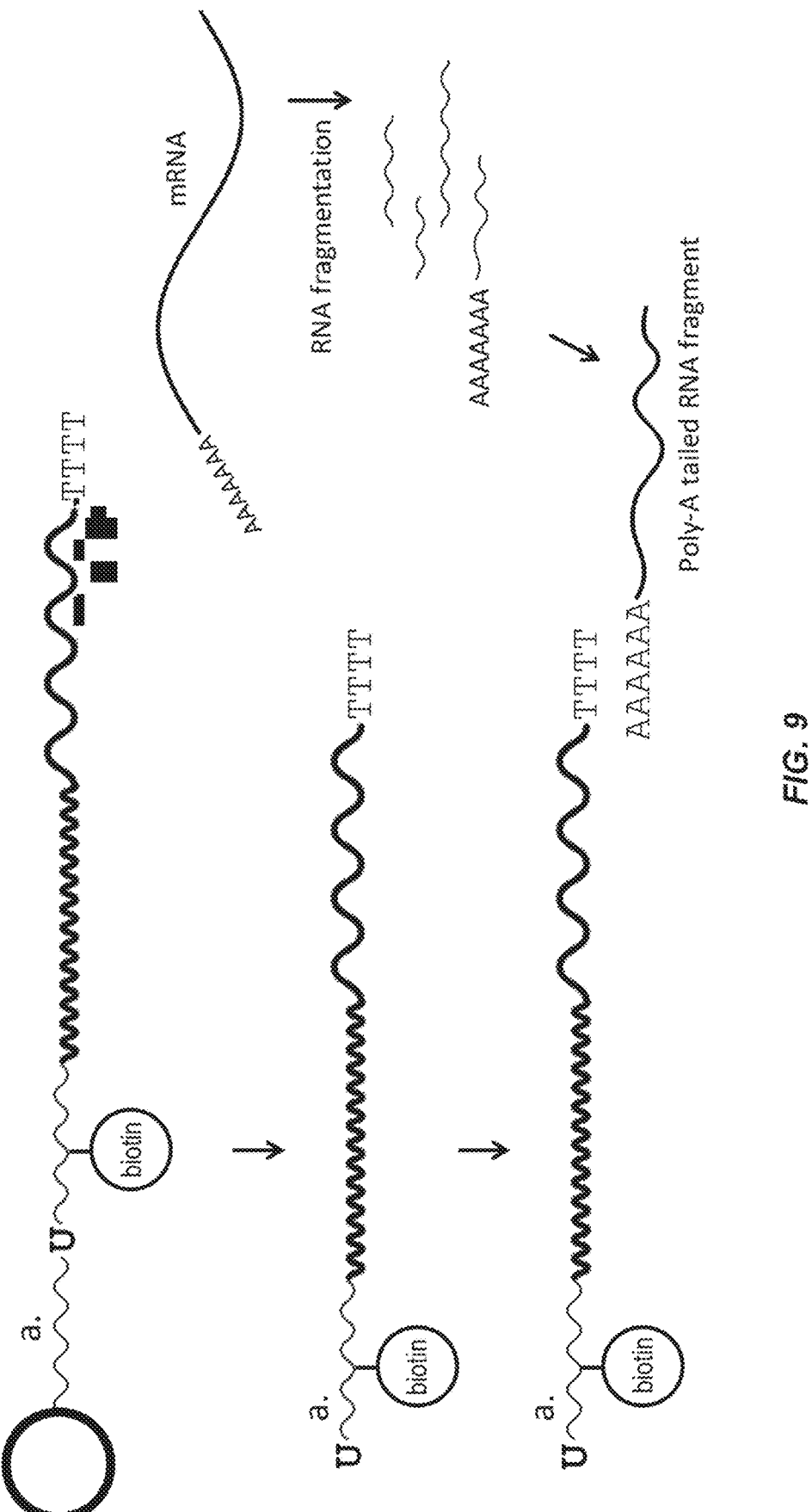
FIG. 9 shows a schematic diagram of bead-oligo release, RNA fragmentation, and RNA-capturing in a partition according to one embodiment described herein. Enzymatic cleavage of barcode-oligos happens at uracil-base(s), and the released soluble barcode-oligos "a" hybridize to poly-A tailed RNA fragments through its 3' end capturing sequence, for example poly-T.

The hybridization can occur in the presence of a DNA polymerase. A "polymerase" refers to an enzyme that performs template-directed synthesis of polynucleotides, e.g., DNA and/or RNA. The term encompasses both the full length polypeptide and a domain that has polymerase activity. DNA polymerases are well-known to those skilled in the art, including but not limited to DNA polymerases isolated or derived from *Pyrococcus furiosus, Thermococcus litoralis*, and *Thermotoga* maritime, or modified versions thereof. In some embodiments, the DNA polymerase does not comprise exonuclease activity to prevent primer degradation. Examples of suitable polymerases include Klenow fragment (New England Biolabs® Inc.), Taq DNA polymerase (QIAGEN), 9° N™ DNA polymerase (New England Biolabs® Inc.), Deep Vent™ DNA polymerase (New England Biolabs® Inc.), Manta DNA polymerase (Enzymatics®), Bst DNA polymerase (New England Biolabs® Inc.), and phi29 DNA polymerase (New England Biolabs® Inc.). Polymerases include both DNA-dependent polymerases and RNA-dependent polymerases such as reverse transcriptase. At least five families of DNA-dependent DNA polymerases are known, although most fall into families A, B and C. Other types of DNA polymerases include phage polymerases. Similarly, RNA polymerases typically include eukaryotic RNA polymerases I, II, and III, and bacterial RNA polymerases as well as phage and viral polymerases. RNA polymerases can be DNA-dependent and RNA-dependent. The DNA polymerase extends the solid support oligonucleotides to generate extended solid support oligonucleotides that comprise a complement of the detector oligonucleotide. In some embodiments, the extended detector solid support oligonucleotides comprise a 3' end that is complementary to the palindromic sequence In some embodiments, the partition comprises reagents for polymerase extension, such as dNTPs and primers, and a UDGase. The UDGase is used to cleave the solid support oligonucleotides comprising the uracil base linker from the solid support (see FIG. 9). Thus, in some embodiments, the method comprises contacting the solid support oligonucleotides with UDGase, thereby cleaving the solid support oligonucleotides from the solid support. In some embodiments, cleavage of the solid support oligonucleotides from the solid support occurs inside the partition.

Figure 10A:
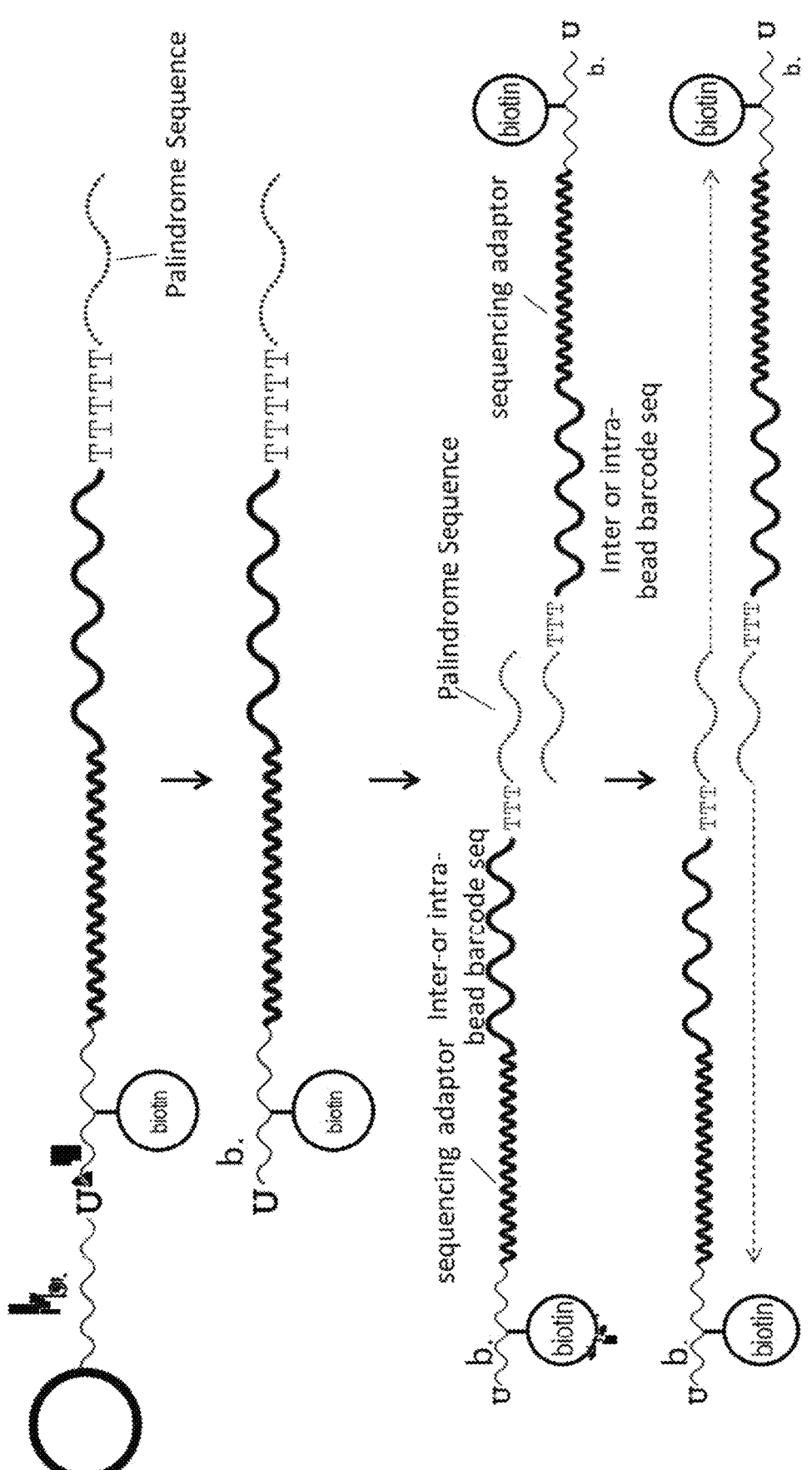
FIG. 10A shows a schematic diagram illustrating bead-oligo release and methods for barcode-oligo joining in a partition according to one embodiment described herein. Enzymatic cleavage of barcode-oligos happens at uracil-base(s), and the released soluble barcode-oligo "b" hybridizes to either a barcode-oligo that originated from its own bead or that of the other beads within the same partition in a random manner. DNA polymerization and extension is carried out by DNA polymerase after the hybridization to form inter and intra barcode-dimers.

In some embodiments, the method further comprises hybridizing the 3' ends of the extended solid support oligonucleotides and extending the 3' ends of the extended detector solid support oligonucleotides with the polymerase, thereby forming double-stranded polynucleotide having barcodes from two of the solid support oligonucleotides (see FIG. 10A).

In some embodiments, the partition comprises a biological sample. In some embodiments, the sample comprises a cell, for example, a single cell, and the method further comprises lysing the cell to release sample nucleic acids, such as RNA. In some embodiments, the cells are lysed during an amplification reaction, and the nucleic acids, such as RNA are fragmented. RNA fragmentation can occur due to the elevated temperatures and $Mg^{++}$ present in the amplification reaction mixture (see FIG. 9).

In some embodiments, the method comprises capturing a sample nucleic acid. In some embodiments, at least some solid support oligonucleotide capture sequences are hybridized to sample nucleic acids and are extended by the polymerase to generate extended sample solid support oligonucleotides that comprise a complement of a sample nucleic acid. In some embodiments, the sample nucleic acid is an mRNA, and the mRNA is captured by hybridizing the poly A tail of the mRNA to the oligo dT sequence on the solid support oligonucleotides. In some embodiments, the reaction that generates the extended sample solid support oligonucleotides occurs inside the partition.

In some aspects, a method for producing a library of nucleic acid molecules for sequencing is described. In some embodiments, the method steps occur inside a partition. The method can comprise providing a plurality of partitions wherein at least some partitions comprise a single cell and multiple solid supports, where different solid supports are linked to first and second solid support oligonucleotides in the same partition. In some embodiments, the first solid support oligonucleotides comprise a barcode unique for the solid support, a capture sequence, and a sequencing adaptor, and the second solid support oligonucleotides comprise a barcode unique for the solid support, a sequencing adaptor, and a palindrome sequence at the 3' end. In some embodiments, the capture sequence comprises poly dT, a random sequence, or a gene-specific sequence.

In some embodiments, the oligonucleotides are released or cleaved from the solid supports, and RNA molecules from a biological sample hybridize to the capture sequence of one or more of the first oligonucleotides to form RNA/oligonucleotide hybrids, and the second solid support oligonucleotides comprising the palindrome sequence hybridize to each other.

The hybridized second solid support oligonucleotides can then be extended using a polymerase to produce double stranded DNA dimer molecules comprising a first and second barcode, where the first and second barcodes are from the same or different solid support oligonucleotides in the same partition. Following extension, the double stranded DNA dimer molecules can be amplified, for example, by PCR, using primers that anneal to the sequencing adaptor. In some embodiments, the amplifying step comprises melting the double stranded DNA molecules and hybridizing primers to the sequencing adaptors, extending the primers using a polymerase, and amplifying the extended molecule by PCR.

Figure 10B:
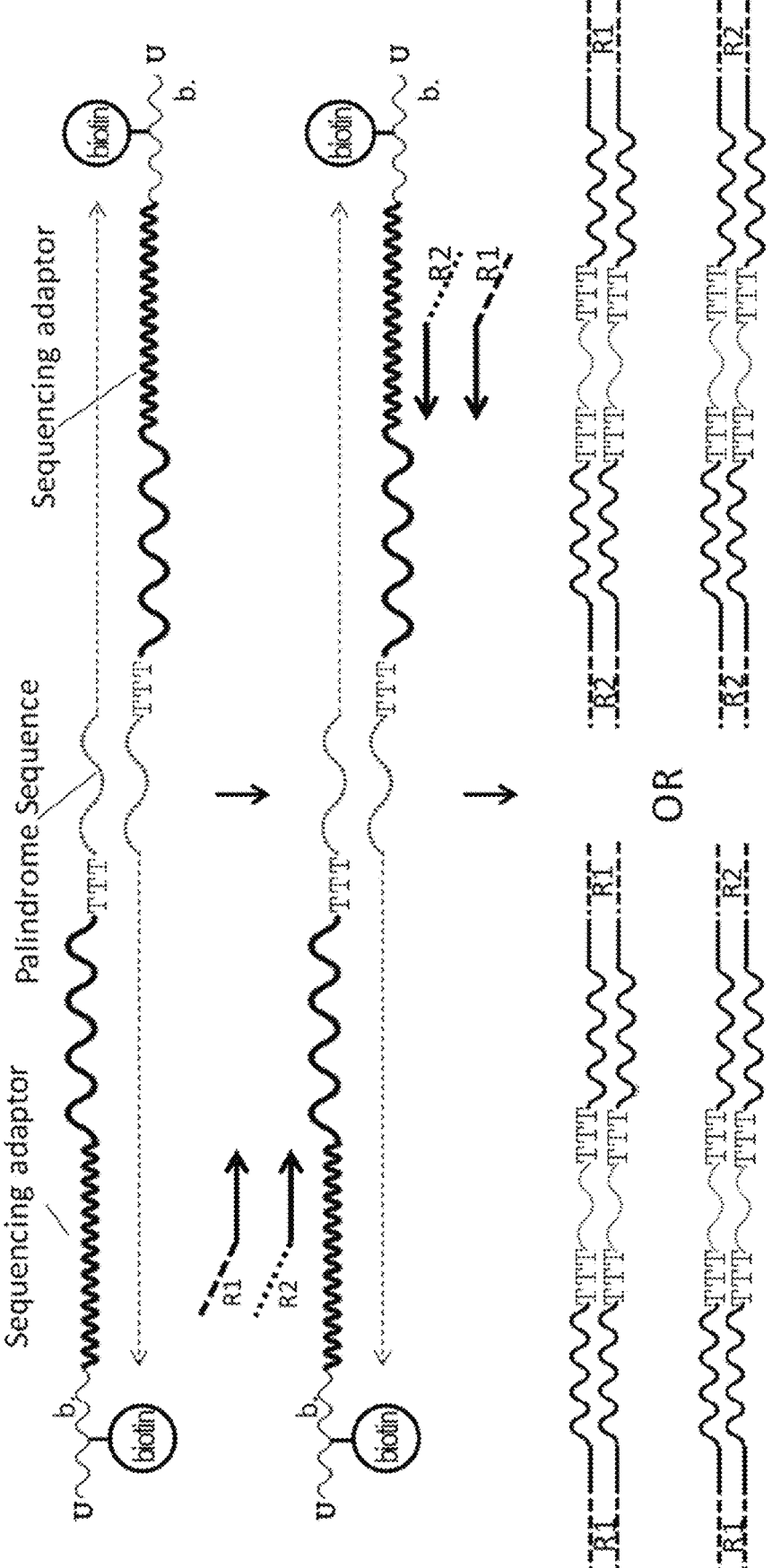
FIG. 10B shows a schematic diagram illustrating adaptor-joining PCR of barcode hybrids according to one embodiment descried herein. The barcode dimer becomes double-stranded after one PCR cycle inside a partition. R1 and R2 sequencing adaptors are then incorporated into the barcode fusion in a subsequent PCR cycle. Due to the 3' sequence commonality, sequencing adaptor primers, R1 and R2, have equal chance of annealing to a region of the Sequencing adaptor sequence on the inter/intra barcode-dimers. As a result, PCR yields a library of 4 products—R1/R1, R1/R2, R2/R1 and R2/R2 as illustrated.

In some embodiments, a mix of primers (e.g., R1 and R2) are used to amplify the double stranded DNA dimer molecules. The R1 and R2 sequencing adaptor primers have common 3' ends, and thus have an equal likelihood of annealing to a complementary region of the sequencing adaptor. See FIG. 10B. Amplification with the primer mix produces a library of 4 different products: R1/R1, R1/R2, R2/R1 and R2/R2. Sequencing PCR products R1/R2 and R2/R1 produces sequence reads from both strands.

Figure 11:
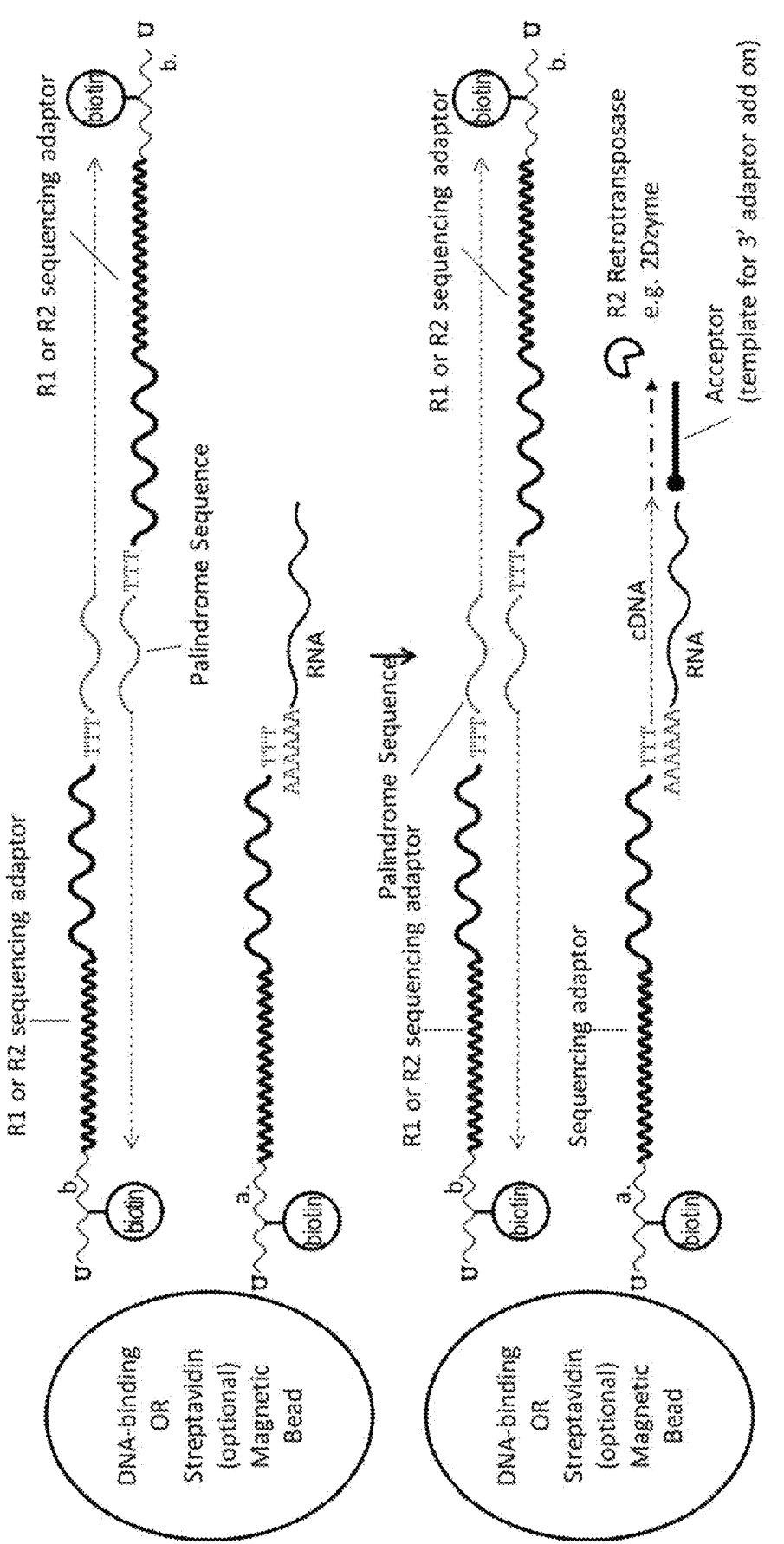
FIG. 11 shows a schematic diagram of barcode oligo capturing, cDNA synthesis, and cDNA 3'-adaptor addition processes in bulk outside a partition. After partition breakage, the RNA/barcode-oligo hybrids and the barcode-dimers are pulled down by DNA-binding magnetic beads or optionally the Streptavidin conjugated magnetic beads if the biotin-labeled nucleotide base(s) is present. The cDNA synthesis and 3'-adaptor addition are carried on by the reverse-transcription and the acceptor extension processes of R2 retrotransposase as illustrated. Fully adaptor cDNA and barcode dimers are amplified and sample indexed by PCR. Following PCR, the library is size-selected and purified before sequence analysis by next-gen sequencing and bioinformatics.

The method can also extend the RNA bound to RNA/first oligonucleotide hybrids to generate cDNA. Reverse transcription of the RNA can be performed using R2 retrotransposase to synthesize cDNA. An acceptor molecule can be added to the reaction to serve as a template for adding a 3' adaptor to the cDNA. The cDNA comprising the 3' adaptor can then be amplified, for example, by PCR. In some embodiments, the RNA/first oligonucleotide hybrids and the double stranded DNA dimer molecules comprising hybridized second solid support oligonucleotides are amplified outside of the partition. See FIG. 11.

In some embodiments, the nucleic acid molecules in the library are sequenced, for example, using next-generation sequencing technology. Sequences comprising the same barcodes indicates the solid supports were present in the same partition.

In another aspect, a method of detecting the presence of multiple barcoded solid supports in partitions is described, the method comprising: a) providing a plurality of partitions wherein at least some partitions comprise multiple solid supports, where each solid support is linked to (i) a plurality of first solid support oligonucleotides comprising a barcode sequence unique for the solid support and a capture sequence; and (ii) one or more second oligonucleotides having a 3' end comprising a sequence complementary to the capture sequence, the barcode sequence and a 5' palindromic sequence; wherein the ratio of first solid support oligonucleotides to second oligonucleotides is at least at least 5:1, 10:1, 100:1, 1000:1, 5000:1, 10000:1, 20000:1; 30000:1. 40000:1, 50000:1; 60000:1, 70000:1; 80000:1, 90000:1, or 100000:1;

b) releasing the first and second oligonucleotides from the solid supports;

c) hybridizing the capture sequence of some of the solid support oligonucleotides to the 3' ends of the second oligonucleotides in the presence of a first polymerase to generate extended solid support oligonucleotides that comprise a complement of the second oligonucleotide, wherein the extended solid support oligonucleotides comprise a 3' end that is complementary to the palindromic sequence; and d) hybridizing the 3' ends of the extended solid support oligonucleotides and extending the 3' ends with a second polymerase, thereby forming double-stranded polynucleotides having barcodes from two of the solid support oligonucleotides. and e) sequencing one or both strands of the double-stranded polynucleotides, wherein sequences comprising two different barcodes indicates the presence of two solid supports in the same partition.

In some embodiments, the sequence complementary to the capture sequence comprises a 3' terminator or is blocked at the 3' end to prevent extension by a polymerase.

In some embodiments, the first polymerase in step (c) does not have exonuclease activity. In some embodiments, the polymerase is a Therminator™ DNA polymerase or a Taq DNA polymerase.

In some embodiments, the first oligonucleotide further comprises one or more of: a) a uracil base; b) a biotin base; or d) an adapter sequence for sequencing reactions.

In any embodiments described herein, the partition can be a droplet in an emulsion or a microwell.

In some embodiments, the biological sample comprises a single cell, and the cell is lysed to release RNA. In some embodiments, the RNA is fragmented to produce RNA fragments. The RNA can be fragmented, for example by heat in the presence of divalent ions, conditions which are present in amplification reactions.

In some embodiments, the partitions comprise a DNA polymerase, divalent ions, sequencing adaptors, deoxynucleotide triphosphates (dNTPs), and primers having at least a 3' sequence complementary to the sequencing adaptors. In some embodiments, the partition further comprises poly(A) polymerase and ATP, and a poly-A tail is added to the RNA fragments.

In some embodiments, the first and/or second oligonucleotide comprises a uracil base, and the oligonucleotide is released from the solid support by contacting the oligonucleotide with a UDGase or USER enzyme.

In some aspects, the methods described herein can be used to capture the 3' end of mRNA molecules, micro RNAs, or total RNA for analysis. In some embodiments, the methods occur in a partition such as an emulsion droplet. In some embodiments, the methods occur in microwell partitions. In some embodiments, the methods can be used with barcoded solid supports described herein.

For example, in one embodiment, the methods allow for capturing the 3' end of mRNAs. In some embodiments, the method comprises releasing the mRNA that is hybridized to the barcode oligonucleotide from the solid support or bead. In some embodiments, the method comprises enzymatic cleavage of the barcode oligonucleotide in order to release the hybridized mRNA from the solid support or bead. In some embodiments, the method comprises enzymatic cleavage of a uracil base in the barcode oligonucleotide by UDGase or USER enzyme. In some embodiments, the mRNA is fragmented either before or after hybridization to the capture barcode oligonucleotide, or after the hybrid molecule is released from the solid support. In some embodiments, the RNA is fragmented by heat in the presence of divalent ions. In some embodiments, the hybridized RNA is used as a template for production of cDNA, e.g., by using a reverse transcriptase, a reverse transcriptase with template switching activity, or R2 retrotransposase. Sequencing adaptors can then be added as described herein. The cDNA can then be used as a template to produce double-stranded DNA comprising barcodes. The double-stranded, barcoded DNA can be sequenced as described herein.

In another embodiment, the methods can be used to capture micro RNAs (miRNA) from cells. Micro RNAs are small non-coding RNA molecules (about 22 nucleotides in length) that function in RNA silencing and post-transcriptional regulation of gene expression. miRNAs do not typically contain a 3' polyadenine (poly(A)) tail. Thus, in some embodiments, the method comprises contacting the RNA isolated from a cell with a poly(A) polymerase (polynucleotide adenylyltransferase) and ATP to add a poly(A) tail to the 3' hydroxyl end of the miRNA. Following the addition of the 3' poly(A) tail, the method can proceed as above to capture and sequence miRNAs.

In another embodiment, the methods can be used to capture total RNA. Total RNA includes RNA that does not have a poly(A) tail, such as transfer RNA (tRNA). In some embodiments, the method comprises fragmenting the RNA with an RNAse, such as RNAse H in the presence of random primers under conditions suitable for hybridization of the primers to the single stranded RNA. The random primers are non-extendable by enzymes such as polymerases, transcriptases, or retrotransposases. The primers hybridize to the RNA at random positions to create short regions of RNA: DNA heteroduplex. The RNA is then contacted with RNAse H to cleave the RNA at the short regions of double-stranded RNA. which creates an extendable 3' end. The 3' ends of the fragmented RNA can then be extended using poly(A) polymerase and ATP to add 3' poly(A) tails. In some embodiments, the random primers comprise an extension blocker, such as a propanediol that prevents extension by a DNA polymerase, that is cleavable by RNAse H. Following the addition of the 3' poly(A) tail, the method can proceed as described above to prepare double-stranded, barcoded DNA for sequencing reactions.

A. Purification

In some embodiments, the emulsion is then broken, releasing the contents of the partition. In some embodiments, the contents of the partitions are combined. In some embodiments, the released solid support oligonucleotides, including the extended sample solid support oligonucleotides, are purified. In some embodiments, the released solid support oligonucleotides are purified by affinity chromatography. In some embodiments, the released solid support oligonucleotides comprise one or a first member of a binding pair, and are purified by binding to the other or second member of the binding pair. Examples of suitable binding pairs include ligands and receptors, antibodies and cognate antigens, and biotin-streptavidin. For example, the released solid support oligonucleotides, including the extended sample solid support oligonucleotides, can comprise biotin, and the solid support oligonucleotides are purified by binding to streptavidin. In some embodiments, the solid support oligonucleotides are purified by binding to a solid support comprising (or linked to) streptavidin. The non-binding components can be removed by washing. In some embodiments, the solid support is magnetic, and the bound solid support oligonucleotides are purified using a magnetic field to separate the bound solid support oligonucleotides from unbound components.

In some embodiments, the solid support oligonucleotides are contacted with a modified transposon enzyme such as 2Dzyme® (2D Genomics) having very high processivity, strand-displacement and built-in reverse transcriptase activity for high conversion efficiency of captured RNA into sequencing libraries. The strands of the double stranded polynucleotides can then be sequenced. If the sequence comprises two different barcodes, this indicates that two different solid supports were present the same partition.

In some embodiments, the bound solid support oligonucleotides are removed from the solid supports, for example by elution. Elution of the oligonucleotides from the beads may involve photocleavage of photocleavible oligonucleotide motifs, proteinase K SDS treatment of protein complexes that link the oligonucleotides to the magnetic bead and/or denaturation of protein complexes that link the oligonucleotides to the magnetic bead using chaotropic reagents such as guanidinium thiocyanate.

B. Tagmentase

Heteroadapter-loaded tagmentases and homoadapter-loaded tagmentases can be used as described herein. Homoadapter-loaded tagmentases are tagmentases that contain adaptors of only one sequence, which adaptor is added to either end of a tagmentase-induced breakpoint in the genomic DNA. Heteroadapter loaded tagmentases are tagmentases that contain two different adaptors, such that a different adaptor sequence is added to the two DNA ends created by a tagmentase-induced breakpoint in the DNA. Adapter loaded tagmentases are further described, e.g., in U.S. Patent Publication Nos: 2010/0120098; 2012/0301925; and 2015/0291942 and U.S. Pat. Nos. 5,965,443; 6,437,109; 7,083,980; 9,005,935; and 9,238,671, the contents of each of which are hereby incorporated by reference in the entirety for all purposes.

A tagmentase is an enzyme that is capable of forming a functional complex with a transposon end-containing composition and catalyzing insertion or transposition of the transposon end-containing composition into the double-stranded target DNA with which it is incubated in an in vitro transposition reaction. Exemplary transposases include but are not limited to modified TN5 transposases that are hyperactive compared to wildtype TN5, for example can have one or more mutations selected from E54K, M56A, or L372P. Wild-type Tn5 transposon is a composite transposon in which two near-identical insertion sequences (IS50L and IS50R) are flanking three antibiotic resistance genes (Reznikoff W S. *Annu Rev Genet* 42: 269-286 (2008)). Each IS50 contains two inverted 19-bp end sequences (ESs), an outside end (OE) and an inside end (IE). However, wild-type ESs have a relatively low activity and were replaced in vitro by hyperactive mosaic end (ME) sequences. A complex of the transposase with the 19-bp ME is thus all that is necessary for transposition to occur, provided that the intervening DNA is long enough to bring two of these sequences close together to form an active Tn5 transposase homodimer (Reznikoff W S., *Mol Microbiol* 47: 1199-1206 (2003)). Transposition is a very infrequent event in vivo, and hyperactive mutants were historically derived by introducing three missense mutations in the 476 residues of the Tn5 protein (E54K, M56A, L372P), which is encoded by IS50R (Goryshin I Y, Reznikoff W S. 1998. *J Biol Chem* 273: 7367-7374 (1998)). Transposition works through a "cut-and-paste" mechanism, where the Tn5 excises itself from the donor DNA and inserts into a target sequence, creating a 9-bp duplication of the target (Schaller H. *Cold Spring Harb Symp Quant Biol* 43: 401-408 (1979); Reznikoff W S., *Annu Rev Genet* 42: 269-286 (2008)). In current commercial solutions (Nextera™ DNA kits, Illumina), free synthetic ME adaptors are end-joined to the 5'-end of the target DNA by the transposase (tagmentase). In some embodiments, the tagmentase is linked to a solid support (e.g., a bead that is different from the bead linked to the forward primer). An example commercial bead-linked tagmentase is Nextera™ DNA Flex (Illumina).

In some embodiments, the adaptor(s) is at least 19 nucleotides in length, e.g., 19-100 nucleotides. In some embodiments, the adapters are double stranded with a 5' end overhang, wherein the 5' overhand sequence is different between heteroadaptors, while the double stranded portion (typically 19 bp) is the same. In some embodiments, an adaptor comprises TCGTCGGCAGCGTC (SEQ ID NO: 3) or GTCTCGTGGGCTCGG (SEQ ID NO: 4). In some embodiments involving the heteroadaptor-loaded tagmentase, the tagmentase is loaded with a first adaptor comprising TCGTCGGCAGCGTC (SEQ ID NO: 3) and a second adaptor comprising GTCTCGTGGGCTCGG (SEQ ID NO: 4). In some embodiments, the adapter comprises AGATGTGTATAAGAGACAG (SEQ ID NO: 1) and the complement thereof (this is the mosaic end and this is the only specifically required cis active sequence for Tn5 transposition). In some embodiments, the adapter comprises TCGTCGGCAGCGTCAGATGTGTATAAGAGACAG (SEQ ID NO: 5) with the complement for AGATGTGTATAAGAGACAG (SEQ ID NO: 1) or GTCTCGTGGGCTCGGAGATGTGTATAAGAGACAG (SEQ ID NO: 6) with the complement for AGATGTGTATAAGAGACAG (SEQ ID NO: 1). In some embodiments involving the heteroadaptor-loaded tagmentase, the tagmentase is loaded with a first adaptor comprising TCGTCGGCAGCGTCAGATGTGTATAAGAGACAG (SEQ ID NO: 5) with the complement for AGATGTGTATAAGAGACAG (SEQ ID NO: 1) and GTCTCGTGGGCTCGGAGATGTGTATAAGAGACAG (SEQ ID NO: 6) with the complement for AGATGTGTATAAGAGACAG (SEQ ID NO: 1).

In some embodiments, the adaptors have a 19 bp double stranded region and a 5' 15 bp single stranded overhang. The sequence of the 15 bp is different between heteroadaptors whereas the double-stranded region has a common sequence between adaptors (homo or heteroadaptors).

In some embodiments, whether the tagmentase is loaded with hetero or homo adaptors, the pair of adaptors can be linked via a linking nucleotide sequence. The linking sequence can be any nucleotide sequence linking the two adaptors. The linking sequence can be, in some embodiments, between 2 nucleotides to 5 kb long. In some embodiments, the linking sequence can contain one or more restriction recognition sequence such that the linking sequence can be cleaved later by a restriction enzyme added to the partitions. To avoid cleavage within the DNA segments themselves, it can be beneficial to select a rare cutting restriction enzyme, for example a restriction enzyme having a recognition sequence having 8 or more nucleotides.

In other embodiments, the linking sequence can contain one or more (e.g., 2, 3, 4, 5, 6, 7, 8, 9, or 10) uracils. The linking sequence can subsequently be cleaved in the presence of uracil-DNA N-glycosylase (e.g., "UNG"), which can be included in the partition.

In other embodiments, the linking sequence can contain one or more (e.g., 2, 3, 4, 5, 6, 7, 8, 9, or 10) ribonucleotides. The linking sequence can subsequently be cleaved in the presence of base or RNase, which can be included in the partition.

Conditions for tagmentation are selected such that the tagmentase creates breakpoints in the DNA and such that adaptors loaded on the tagmentase are added to either end of the breakpoint. The tagmentase introduces a single-stranded adaptor sequence on either end of the breakpoint, forming a 5' overhang. The 5' overhang is then filled ("gap filled") by a polymerase to create a double-stranded sequence at either end of the DNA segments. See, e.g., FIG. 9. The non-transferred bottom strand is thus rendered contiguous and complementary to the transferred top strand. This contiguous bottom strand is now compatible with polymerase extension reactions, e.g., PCR. Thus "gap filling" is the process after tagmentation that renders the bottom strand (the one that is not transferred) contiguous with the top strand at the end of the DNA segments. Gap filling refers to reconstitution of the bottom strand. This is done preferentially by a DNA polymerase that extends back from the 3' of the bottom non-transferred strand that is upstream of the gap. The polymerase that gap fills can either have 5' to 3' exo activity or strand displacing activity to help overcome the non-transferred mosaic end. Neither gap filling nor adding of the barcode involves ligation.

Conditions are also selected such that the tagmentase remains bound to the DNA breakpoints thereby maintaining contiguity. Tagmentase has been observed to remain bound to DNA until a detergent such as SDS is added to the reaction (Amini et al. *Nature Genetics* 46(12):1343-1349).

C. Partitions

Any type of partition can be used in the methods described herein. While the method has been exemplified using droplets it should be understood that other types of partitions can also be used.

In some embodiments, the partitions contain a first oligonucleotide linked to a first solid support and a second oligonucleotide linked to a second solid support.

Methods and compositions for partitioning are described, for example, in published patent applications WO 2010/036, 352, US 2010/0173,394, US 2011/0092,373, and US 2011/0092,376, the contents of each of which are incorporated herein by reference in the entirety. The plurality of mixture partitions can be in a plurality of emulsion droplets, or a plurality of microwells, etc.

In some embodiments, the primers and other reagents can be partitioned into a plurality of mixture partitions, and then linked DNA segments can be introduced into the plurality of mixture partitions. Methods and compositions for delivering reagents to one or more mixture partitions include microfluidic methods as known in the art; droplet or microcapsule merging, coalescing, fusing, bursting, or degrading (e.g., as described in U.S. 2015/0027,892; US 2014/0227,684; WO 2012/149,042; and WO 2014/028,537); droplet injection methods (e.g., as described in WO 2010/151,776); and combinations thereof.

As described herein, the mixture partitions can be picowells, nanowells, or microwells. The mixture partitions can be pico-, nano-, or micro-reaction chambers, such as pico, nano, or microcapsules. The mixture partitions can be pico-, nano-, or micro-channels. The mixture partitions can be droplets, e.g., emulsion droplets.

In some embodiments, the partitions are droplets. In some embodiments, a droplet comprises an emulsion composition, i.e., a mixture of immiscible fluids (e.g., water and oil). In some embodiments, a droplet is an aqueous droplet that is surrounded by an immiscible carrier fluid (e.g., oil). In some embodiments, a droplet is an oil droplet that is surrounded by an immiscible carrier fluid (e.g., an aqueous solution). In some embodiments, the droplets described herein are relatively stable and have minimal coalescence between two or more droplets. In some embodiments, less than 0.0001%, 0.0005%, 0.001%, 0.005%, 0.01%, 0.05%, 0.1%, 0.5%, 1%, 2%, 3%, 4%, 5%, 6%, 7%, 8%, 9%, or 10% of droplets generated from a sample coalesce with other droplets. The emulsions can also have limited flocculation, a process by which the dispersed phase comes out of suspension in flakes. In some cases, such stability or minimal coalescence is maintained for up to 4, 6, 8, 10, 12, 24, or 48 hours or more (e.g., at room temperature, or at about 0, 2, 4, 6, 8, 10, or 12° C.). In some embodiments, the droplet is formed by flowing an oil phase through an aqueous sample or reagents.

The oil phase can comprise a fluorinated base oil which can additionally be stabilized by combination with a fluorinated surfactant such as a perfluorinated polyether. In some embodiments, the base oil comprises one or more of a HFE 7500, FC-40, FC-43, FC-70, or another common fluorinated oil. In some embodiments, the oil phase comprises an anionic fluorosurfactant. In some embodiments, the anionic fluorosurfactant is Ammonium Krytox (Krytox-AS), the ammonium salt of Krytox FSH, or a morpholino derivative of Krytox FSH. Krytox-AS can be present at a concentration of about 0.1%, 0.2%, 0.3%, 0.4%, 0.5%, 0.6%, 0.7%, 0.8%, 0.9%, 1.0%, 2.0%, 3.0%, or 4.0% (w/w). In some embodiments, the concentration of Krytox-AS is about 1.8%. In some embodiments, the concentration of Krytox-AS is about 1.62%. Morpholino derivative of Krytox FSH can be present at a concentration of about 0.1%, 0.2%, 0.3%, 0.4%, 0.5%, 0.6%, 0.7%, 0.8%, 0.9%, 1.0%, 2.0%, 3.0%, or 4.0% (w/w). In some embodiments, the concentration of morpholino derivative of Krytox FSH is about 1.8%. In some embodiments, the concentration of morpholino derivative of Krytox FSH is about 1.62%.

In some embodiments, the oil phase further comprises an additive for tuning the oil properties, such as vapor pressure, viscosity, or surface tension. Non-limiting examples include perfluorooctanol and 1H,1H,2H,2H-Perfluorodecanol. In some embodiments, 1H,1H,2H,2H-Perfluorodecanol is added to a concentration of about 0.05%, 0.06%, 0.07%, 0.08%, 0.09%, 0.1%, 0.2%, 0.3%, 0.4%, 0.5%, 0.6%, 0.7%, 0.8%, 0.9%, 1.0%, 1.25%, 1.50%, 1.75%, 2.0%, 2.25%, 2.5%, 2.75%, or 3.0% (w/w). In some embodiments, 1H,1H, 2H,2H-Perfluorodecanol is added to a concentration of about 0.18% (w/w).

In some embodiments, the emulsion is formulated to produce highly monodisperse droplets having a liquid-like interfacial film that can be converted by heating into microcapsules having a solid-like interfacial film; such microcapsules can behave as bioreactors able to retain their contents through an incubation period. The conversion to microcapsule form can occur upon heating. For example, such conversion can occur at a temperature of greater than about 40°, 50°, 60°, 70°, 80°, 90°, or 95° C. During the heating process, a fluid or mineral oil overlay can be used to prevent evaporation. Excess continuous phase oil can be removed prior to heating, or left in place. The microcapsules can be resistant to coalescence and/or flocculation across a wide range of thermal and mechanical processing.

Following conversion of droplets into microcapsules, the microcapsules can be stored at about −70°, −20°, 0°, 3°, 4°, 5°, 6°, 7°, 8°, 9°, 10°, 15°, 20°, 25°, 30°, 35°, or 40° C. In some embodiments, these capsules are useful for storage or transport of partition mixtures. For example, samples can be collected at one location, partitioned into droplets containing enzymes, buffers, and/or primers or other probes, optionally one or more polymerization reactions can be performed, the partitions can then be heated to perform microencapsulation, and the microcapsules can be stored or transported for further analysis.

In some embodiments, the sample is partitioned into, or into at least, 500 partitions, 1000 partitions, 2000 partitions, 3000 partitions, 4000 partitions, 5000 partitions, 6000 partitions, 7000 partitions, 8000 partitions, 10,000 partitions, 15,000 partitions, 20,000 partitions, 30,000 partitions, 40,000 partitions, 50,000 partitions, 60,000 partitions, 70,000 partitions, 80,000 partitions, 90,000 partitions, 100, 000 partitions, 200,000 partitions, 300,000 partitions, 400, 000 partitions, 500,000 partitions, 600,000 partitions, 700, 000 partitions, 800,000 partitions, 900,000 partitions, 1,000, 000 partitions, 2,000,000 partitions, 3,000,000 partitions, 4,000,000 partitions, 5,000,000 partitions, 10,000,000 partitions, 20,000,000 partitions, 30,000,000 partitions, 40,000, 000 partitions, 50,000,000 partitions, 60,000,000 partitions, 70,000,000 partitions, 80,000,000 partitions, 90,000,000 partitions, 100,000,000 partitions, 150,000,000 partitions, or 200,000,000 partitions.

In some embodiments, the droplets that are generated are substantially uniform in shape and/or size. For example, in some embodiments, the droplets are substantially uniform in average diameter. In some embodiments, the droplets that are generated have an average diameter of about 0.001 microns, about 0.005 microns, about 0.01 microns, about 0.05 microns, about 0.1 microns, about 0.5 microns, about 1 microns, about 5 microns, about 10 microns, about 20 microns, about 30 microns, about 40 microns, about 50 microns, about 60 microns, about 70 microns, about 80 microns, about 90 microns, about 100 microns, about 150 microns, about 200 microns, about 300 microns, about 400 microns, about 500 microns, about 600 microns, about 700 microns, about 800 microns, about 900 microns, or about 1000 microns. In some embodiments, the droplets that are generated have an average diameter of less than about 1000 microns, less than about 900 microns, less than about 800 microns, less than about 700 microns, less than about 600 microns, less than about 500 microns, less than about 400 microns, less than about 300 microns, less than about 200 microns, less than about 100 microns, less than about 50 microns, or less than about 25 microns. In some embodiments, the droplets that are generated are non-uniform in shape and/or size.

In some embodiments, the droplets that are generated are substantially uniform in volume. For example, the standard deviation of droplet volume can be less than about 1 picoliter, 5 picoliters, 10 picoliters, 100 picoliters, 1 nL, or less than about 10 nL. In some cases, the standard deviation of droplet volume can be less than about 10-25% of the average droplet volume. In some embodiments, the droplets that are generated have an average volume of about 0.001 nL, about 0.005 nL, about 0.01 nL, about 0.02 nL, about 0.03 nL, about 0.04 nL, about 0.05 nL, about 0.06 nL, about 0.07 nL, about 0.08 nL, about 0.09 nL, about 0.1 nL, about 0.2 nL, about 0.3 nL, about 0.4 nL, about 0.5 nL, about 0.6 nL, about 0.7 nL, about 0.8 nL, about 0.9 nL, about 1 nL, about 1.5 nL, about 2 nL, about 2.5 nL, about 3 nL, about 3.5 nL, about 4 nL, about 4.5 nL, about 5 nL, about 5.5 nL, about 6 nL, about 6.5 nL, about 7 nL, about 7.5 nL, about 8 nL, about 8.5 nL, about 9 nL, about 9.5 nL, about 10 nL, about 11 nL, about 12 nL, about 13 nL, about 14 nL, about 15 nL, about 16 nL, about 17 nL, about 18 nL, about 19 nL, about 20 nL, about 25 nL, about 30 nL, about 35 nL, about 40 nL, about 45 nL, or about 50 nL.

As noted above, the partitions will include one or a few (e.g., 1, 2, 3, 4) beads per partition, where in each bead is linked to a first oligonucleotide primer having a free 3' end. The first oligonucleotide primer will have a bead-specific barcode and a 3' end that is complementary to an adaptor. In some embodiments, the barcode will be, e.g., 2-10 nucleotides in length, e.g., 2, 3, 4, 5, 6, 7, 8, 9, or 10 nucleotides. The barcode can be continuous or discontinuous, i.e., broken up by other nucleotides. In some embodiments, the 3' end will be complementary to the entire adaptor sequence. In some embodiments, at least the 3'-most 6, 7, 8, 9, 10, 11, 12, 13, 14, 15, 16, 17, 18, 19, or 20 of the oligonucleotide are complementary to a sequence in the adaptor. In some embodiments, the first oligonucleotide primer further comprises a universal or other additional sequence to assist with downstream manipulation or sequencing of the amplicon. For example, when Illumina-based sequencing is used the first oligonucleotide primer can have a 5' P5 or P7 sequence (optionally with the second oligonucleotide primer having the other of the two sequences). Optionally, the first oligonucleotide primer comprises a restriction or cleavage site to remove the first oligonucleotide primer from the bead when desired. In some embodiments, once the DNA segments are in the partitions with the bead-linked first oligonucleotide primer, the first oligonucleotide primer is cleaved from the bead prior to amplification.

The term "bead" refers to any solid support that can be in a partition, e.g., a small particle or other solid support.

Exemplary beads can include hydrogel beads. In some cases, the hydrogel is in sol form. In some cases, the hydrogel is in gel form. An exemplary hydrogel is an agarose hydrogel. Other hydrogels include, but are not limited to, those described in, e.g., U.S. Pat. Nos. 4,438,258; 6,534,083; 8,008,476; 8,329,763; U.S. Patent Appl. Nos. 2002/0,009, 591; 2013/0,022,569; 2013/0,034,592; and International Patent Publication Nos. WO/1997/030092; and WO/2001/049240.

Methods of linking oligonucleotides to beads are described in, e.g., WO 2015/200541 and U.S. Patent Publication US2016/006,0621 A1. In some embodiments, the oligonucleotide configured to link the hydrogel to the barcode is covalently linked to the hydrogel. Numerous methods for covalently linking an oligonucleotide to one or more hydrogel matrices are known in the art. As but one example, aldehyde derivatized agarose can be covalently linked to a 5'-amine group of a synthetic oligonucleotide.

In some embodiments, the partitions can also contain a second oligonucleotide primer, which can optionally be linked to the bead, or not. This primer can function as a reverse primer for the first oligonucleotide primer such that the two oligonucleotides generate an amplicon in PCR. The second oligonucleotide primer will have a 3' end that is complementary to an adaptor sequence, i.e., the adaptor sequence at the opposite end of the DNA segment compared to the adaptor sequence targeted by the first oligonucleotide primer. In some embodiments, the 3' end will be complementary to the entire adaptor sequence. In some embodiments, at least the 3'-most 6, 7, 8, 9, 10, 11, 12, 13, 14, 15, 16, 17, 18, 19, or 20 of the oligonucleotide are complementary to a sequence in the adaptor. The second oligonucleotide primer can also contain a universal or other additional sequence to assist with downstream manipulation or sequencing of the amplicon. For example, when Illumina-based sequencing is used the second oligonucleotide primer can have a 5' P5 or P7 sequence for binding to the Illumina flow cell (optionally with the first oligonucleotide primer having the other of the two sequences).

Prior to amplification, one can remove or cleave the first oligonucleotide primer from the bead. This can be achieved by any method as desired. Methods of cleaving include, but are not limited to altering the pH or contacting the oligonucleotides with UDG/ApeI or a restriction endonuclease. In some embodiments, the oligonucleotide is linked to the bead via one or more uracils (Us) and USER enzyme (e.g., from NEB) is used to cleave the Us incorporated in the oligo backbone. USER has 2 enzymes: UDG and Endonuclease VIII. In some cases, the oligonucleotides are attached to a solid support through a disulfide linkage (e.g., through a disulfide bond between a sulfide of the solid support and a sulfide covalently attached to the 5' or 3' end, or an intervening nucleic acid, of the oligonucleotide). In such cases, the oligonucleotide can be cleaved from the solid support by contacting the solid support with a reducing agent such as a thiol or phosphine reagent, including but not limited to a beta mercaptoethanol, dithiothreitol (DTT), or tris(2-carboxyethyl)phosphine (TCEP). It can be advantageous to release the first oligonucleotide primer from the bead for a number of reasons. For example, thermodynamics of DNA interactions will greatly increase.

Amplification can be achieved within the partitions (before combining the contents to the partitions). Various digital amplification method are known and can be used.

Following amplification, the contents of the partitions are combined and sequenced. Any method of nucleotide sequencing can be used as desired so long as at least some of the DNA segments sequence and the barcode sequence is determined. Methods for high throughput sequencing and genotyping are known in the art. For example, such sequencing technologies include, but are not limited to, pyrosequencing, sequencing-by-ligation, single molecule sequencing, sequence-by-synthesis (SBS), massive parallel clonal, massive parallel single molecule SBS, massive parallel single molecule real-time, massive parallel single molecule real-time nanopore technology, etc. Morozova and Marra provide a review of some such technologies in Genomics, 92: 255 (2008), herein incorporated by reference in its entirety.

Exemplary DNA sequencing techniques include fluorescence-based sequencing methodologies (See, e.g., Birren et al., Genome Analysis: Analyzing DNA, 1, Cold Spring Harbor, N.Y.; herein incorporated by reference in its entirety). In some embodiments, automated sequencing techniques understood in that art are utilized. In some embodiments, the present technology provides parallel sequencing of partitioned amplicons (PCT Publication No. WO 2006/0841,32, herein incorporated by reference in its entirety). In some embodiments, DNA sequencing is achieved by parallel oligonucleotide extension (See, e.g., U.S. Pat. Nos. 5,750,341; and 6,306,597, both of which are herein incorporated by reference in their entireties). Additional examples of sequencing techniques include the Church polony technology (Mitra et al., 2003, Analytical Biochemistry 320, 55-65; Shendure et al., 2005 Science 309, 1728-1732; and U.S. Pat. Nos. 6,432,360; 6,485,944; 6,511, 803; herein incorporated by reference in their entireties), the 454 picotiter pyrosequencing technology (Margulies et al., 2005 Nature 437, 376-380; U.S. Publication No. 2005/0130173; herein incorporated by reference in their entireties), the Solexa single base addition technology (Bennett et al., 2005, Pharmacogenomics, 6, 373-382; U.S. Pat. Nos. 6,787,308; and 6,833,246; herein incorporated by reference in their entireties), the Lynx massively parallel signature sequencing technology (Brenner et al. (2000). Nat. Biotechnol. 18:630-634; U.S. Pat. Nos. 5,695,934; 5,714,330; herein incorporated by reference in their entireties), and the Adessi PCR colony technology (Adessi et al. (2000). Nucleic Acid Res. 28, E87; WO 2000/018957; herein incorporated by reference in its entirety).

Typically, high throughput sequencing methods share the common feature of massively parallel, high-throughput strategies, with the goal of lower costs in comparison to older sequencing methods (See, e.g., Voelkerding et al., Clinical Chem., 55: 641-658, 2009; MacLean et al., Nature Rev. Microbiol., 7:287-296; each herein incorporated by reference in their entirety). Such methods can be broadly divided into those that typically use template amplification and those that do not. Amplification-requiring methods include pyrosequencing commercialized by Roche as the 454 technology platforms (e.g., GS 20 and GS FLX), the Solexa platform commercialized by Illumina, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and platforms commercialized by VisiGen, Oxford Nanopore Technologies Ltd., Life Technologies/Ion Torrent, and Pacific Biosciences, respectively.

In pyrosequencing (Voelkerding et al., Clinical Chem., 55: 641-658, 2009; MacLean et al., Nature Rev. Microbial., 7:287-296; U.S. Pat. Nos. 6,210,891; and 6,258,568; each herein incorporated by reference in its entirety), template DNA is fragmented, end-repaired, ligated to adaptors, and clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picotitre plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and $10^6$ sequence reads can be achieved, resulting in up to 500 million base pairs (Mb) of sequence.

In the Solexa/Illumina platform (Voelkerding et al., Clinical Chem., 55. 641-658, 2009; MacLean et al., Nature Rev. Microbial., 7:287-296; U.S. Pat. Nos. 6,833,246; 7,115,400; and 6,969,488; each herein incorporated by reference in its entirety), sequencing data are produced in the form of shorter-length reads. In this method, single-stranded fragmented DNA is end-repaired to generate 5'-phosphorylated blunt ends, followed by Klenow-mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluor and block removed prior to the next cycle of dNTP addition. Sequence read length ranges from 36 nucleotides to over 50 nucleotides, with overall output exceeding 1 billion nucleotide pairs per analytical run.

Sequencing nucleic acid molecules using SOLiD technology (Voelkerding et al., Clinical Chem., 55: 641-658, 2009; MacLean et al., Nature Rev. Microbial., 7:287-296; U.S. Pat. Nos. 5,912,148; and 6,130,073; each herein incorporated by reference in their entirety) also involves fragmentation of the template, ligation to oligonucleotide adaptors, attachment to beads, and clonal amplification by emulsion PCR. Following this, beads bearing template are immobilized on a derivatized surface of a glass flow-cell, and a primer complementary to the adaptor oligonucleotide is annealed. However, rather than utilizing this primer for 3' extension, it is instead used to provide a 5' phosphate group for ligation to interrogation probes containing two probe-specific bases followed by 6 degenerate bases and one of four fluorescent labels. In the SOLiD system, interrogation probes have 16 possible combinations of the two bases at the 3' end of each probe, and one of four fluors at the 5' end. Fluor color, and thus identity of each probe, corresponds to specified color-space coding schemes. Multiple rounds (usually 7) of probe annealing, ligation, and fluor detection are followed by denaturation, and then a second round of sequencing using a primer that is offset by one base relative to the initial primer. In this manner, the template sequence can be computationally re-constructed, and template bases are interrogated twice, resulting in increased accuracy. Sequence read length averages 35 nucleotides, and overall output exceeds 4 billion bases per sequencing run.

In certain embodiments, nanopore sequencing is employed (See, e.g., Astier et al., J. Am. Chem. Soc. 2006 Feb. 8; 128(5)1705-10, herein incorporated by reference). The theory behind nanopore sequencing has to do with what occurs when a nanopore is immersed in a conducting fluid and a potential (voltage) is applied across it. Under these conditions a slight electric current due to conduction of ions through the nanopore can be observed, and the amount of current is exceedingly sensitive to the size of the nanopore. As each base of a nucleic acid passes through the nanopore, this causes a change in the magnitude of the current through the nanopore that is distinct for each of the four bases, thereby allowing the sequence of the DNA molecule to be determined.

In certain embodiments, HeliScope by Helicos BioSciences is employed (Voelkerding et al., *Clinical Chem.*, 55. 641-658, 2009; MacLean et al., *Nature Rev. Microbial,* 7:287-296; U.S. Pat. Nos. 7,169,560; 7,282,337; 7,482,120; 7,501,245; 6,818,395; 6,911,345; and 7,501,245; each herein incorporated by reference in their entirety). Template DNA is fragmented and polyadenylated at the 3' end, with the final adenosine bearing a fluorescent label. Denatured polyadenylated template fragments are ligated to poly(dT) oligonucleotides on the surface of a flow cell. Initial physical locations of captured template molecules are recorded by a CCD camera, and then label is cleaved and washed away. Sequencing is achieved by addition of polymerase and serial addition of fluorescently-labeled dNTP reagents. Incorporation events result in fluor signal corresponding to the dNTP, and signal is captured by a CCD camera before each round of dNTP addition. Sequence read length ranges from 25-50 nucleotides, with overall output exceeding 1 billion nucleotide pairs per analytical run.

The Ion Torrent technology is a method of DNA sequencing based on the detection of hydrogen ions that are released during the polymerization of DNA (See, e.g., Science 327 (5970): 1190 (2010); U.S. Pat. Appl. Pub. Nos. 2009/ 0026082; 2009/0127589; 2010/0301398; 2010/0197507; 2010/0188073; and 2010/0137143, incorporated by reference in their entireties for all purposes). A microwell contains a template DNA strand to be sequenced. Beneath the layer of microwells is a hypersensitive ISFET ion sensor. All layers are contained within a CMOS semiconductor chip, similar to that used in the electronics industry. When a dNTP is incorporated into the growing complementary strand a hydrogen ion is released, which triggers the hypersensitive ion sensor. If homopolymer repeats are present in the template sequence, multiple dNTP molecules will be incorporated in a single cycle. This leads to a corresponding number of released hydrogens and a proportionally higher electronic signal. This technology differs from other sequencing technologies in that no modified nucleotides or optics are used. The per base accuracy of the Ion Torrent sequencer is ~99.6% for 50 base reads, with ~100 Mb generated per run. The read-length is 100 base pairs. The accuracy for homopolymer repeats of 5 repeats in length is ~98%. The benefits of ion semiconductor sequencing are rapid sequencing speed and low upfront and operating costs.

Another exemplary nucleic acid sequencing approach that may be adapted for use with the present invention was developed by Stratos Genomics, Inc. and involves the use of Xpandomers. This sequencing process typically includes providing a daughter strand produced by a template-directed synthesis. The daughter strand generally includes a plurality of subunits coupled in a sequence corresponding to a contiguous nucleotide sequence of all or a portion of a target nucleic acid in which the individual subunits comprise a tether, at least one probe or nucleobase residue, and at least one selectively cleavable bond. The selectively cleavable bond(s) is/are cleaved to yield an Xpandomer of a length longer than the plurality of the subunits of the daughter strand. The Xpandomer typically includes the tethers and reporter elements for parsing genetic information in a sequence corresponding to the contiguous nucleotide sequence of all or a portion of the target nucleic acid. Reporter elements of the Xpandomer are then detected. Additional details relating to Xpandomer-based approaches are described in, for example, U.S. Pat. Pub No. 2009/ 0035777, which is incorporated herein in its entirety.

Other single molecule sequencing methods include real-time sequencing by synthesis using a VisiGen platform (Voelkerding et al., Clinical Chem., 55: 641-58, 2009; U.S. Pat. No. 7,329,492; and U.S. patent application Ser. Nos. 11/671,956; and 11/781,166; each herein incorporated by reference in their entirety) in which immobilized, primed DNA template is subjected to strand extension using a fluorescently-modified polymerase and florescent acceptor molecules, resulting in detectible fluorescence resonance energy transfer (FRET) upon nucleotide addition.

Another real-time single molecule sequencing system developed by Pacific Biosciences (Voelkerding et al., Clinical Chem., 55. 641-658, 2009; MacLean et al., Nature Rev. Microbiol., 7:287-296; U.S. Pat. Nos. 7,170,050; 7,302,146; 7,313,308; and 7,476,503; all of which are herein incorporated by reference) utilizes reaction wells 50-100 nm in diameter and encompassing a reaction volume of approximately 20 zeptoliters ($10^{-21}$ L). Sequencing reactions are performed using immobilized template, modified phi29 DNA polymerase, and high local concentrations of fluorescently labeled dNTPs. High local concentrations and continuous reaction conditions allow incorporation events to be captured in real time by fluor signal detection using laser excitation, an optical waveguide, and a CCD camera.

In certain embodiments, the single molecule real time (SMRT) DNA sequencing methods using zero-mode waveguides (ZMWs) developed by Pacific Biosciences, or similar methods, are employed. With this technology, DNA sequencing is performed on SMRT chips, each containing thousands of zero-mode waveguides (ZMWs). A ZMW is a hole, tens of nanometers in diameter, fabricated in a 100 nm metal film deposited on a silicon dioxide substrate. Each ZMW becomes a nanophotonic visualization chamber providing a detection volume of just 20 zeptoliters ($10^{-21}$ L). At this volume, the activity of a single molecule can be detected amongst a background of thousands of labeled nucleotides. The ZMW provides a window for watching DNA polymerase as it performs sequencing by synthesis. Within each chamber, a single DNA polymerase molecule is attached to the bottom surface such that it permanently resides within the detection volume. Phospholinked nucleotides, each type labeled with a different colored fluorophore, are then introduced into the reaction solution at high concentrations which promote enzyme speed, accuracy, and processivity. Due to the small size of the ZMW, even at these high concentrations, the detection volume is occupied by nucleotides only a small fraction of the time. In addition, visits to the detection volume are fast, lasting only a few microseconds, due to the very small distance that diffusion has to carry the nucleotides. The result is a very low background.

Processes and systems for such real time sequencing that may be adapted for use with the invention are described in, for example, U.S. Pat. Nos. 7,405,281; 7,315,019; 7,313, 308; 7,302,146; and 7,170,050; and U.S. Pat. Pub. Nos. 2008/0212960; 2008/0206764; 2008/0199932; 2008/ 0199874; 2008/0176769; 2008/0176316; 2008/0176241; 2008/0165346; 2008/0160531; 2008/0157005; 2008/ 0153100; 2008/0153095; 2008/0152281; 2008/0152280; 2008/0145278; 2008/0128627; 2008/0108082; 2008/ 0095488; 2008/0080059; 2008/0050747; 2008/0032301; 2008/0030628; 2008/0009007; 2007/0238679; 2007/ 0231804; 2007/0206187; 2007/0196846; 2007/0188750; 2007/0161017; 2007/0141598; 2007/0134128; 2007/ 0128133; 2007/0077564; 2007/0072196; and 2007/ 0036511; and Korlach et al. (2008) "Selective aluminum passivation for targeted immobilization of single DNA polymerase molecules in zero-mode waveguide nanostructures" PNAS 105(4): 1176-81, all of which are herein incorporated by reference in their entireties.

In some embodiments, at least some partitions further comprise a sample (e.g., one or more target nucleic acids, or one or more cells). In some embodiments, the sample comprising target nucleic acids comprises DNA, RNA, or a combination or hybrid thereof. In some embodiments, the sample is a sample comprising cells, e.g., is a single-cell sample.

In some embodiments, the partitions further comprise additional reagents or components for polymerization, amplification, reverse transcription, or primer extension (e.g., polymerases, salts, nucleotides, buffers, stabilizers, primers, detectable agents, or nuclease-free water).

Compositions

In one aspect, provided are compositions comprising barcoded solid supports described herein, where each solid support is linked or attached to a different oligonucleotide (a solid support oligonucleotide) than other solid supports. In some embodiments, the solid support oligonucleotide comprises a barcode unique for the solid support to which it is attached (a barcode oligonucleotide). In some embodiments, the composition comprises a first solid support attached to a first solid support oligonucleotide comprising a first barcode unique for the first solid support, and a second solid support attached to a second solid support oligonucleotide comprising a second barcode unique for the second solid support.

In some embodiments, the composition comprises a solid support linked or attached to two or more different oligonucleotides (e.g., two or more solid support oligonucleotides). The two or more oligonucleotides can comprise: (i) a plurality of first oligonucleotides comprising a barcode unique for the solid support, a capture sequence, and a sequencing adaptor; and (ii) one or more second oligonucleotides comprising a barcode unique for the solid support, a sequencing adaptor, and a palindrome sequence at the 3' end. In some embodiments, the ratio of first oligonucleotides to second oligonucleotides is at least 5:1, 10:1, 100:1, 1000:1, 5000:1, 10000:1, 20000:1; 30000:1. 40000:1, 50000:1; 60000:1, 70000:1; 80000:1, 90000:1 or 100000:1. In some embodiments, the second oligonucleotide also comprises a capture sequence.

In some embodiments, the capture sequence is located at the 3' end of the first and second oligonucleotides. In some embodiments, the capture sequence is a poly dT sequence. In some embodiments, the capture sequence is a random sequence. In some embodiments, the capture sequence is a gene-specific sequence.

In some embodiments, the composition comprises a solid support is linked to (i) a plurality of first solid support oligonucleotides comprising a barcode sequence unique for the solid support and a capture sequence; and (ii) a plurality of second oligonucleotides having a 3' end comprising a sequence complementary to the capture sequence, the barcode sequence, and a 5' palindromic sequence. In some embodiments, the first solid support oligonucleotides and the second oligonucleotides comprise the same barcode sequence.

In any of the embodiments described herein, the ratio of first solid support oligonucleotides to second oligonucleotides is at least 5:1, 10:1, 100:1, 1000:1, 5000:1, 10000:1, 20000:1; 30000:1. 40000:1, 50000:1; 60000:1, 70000:1; 80000:1, 90000:1 or 100000:1.

In some embodiments, the palindromic sequence is 4-250 nucleotides in length, or any sub-range therein, for example, 4-80, 10-20, 10-30, 10-40, 20-30, or 20-40 nucleotides in length.

In some embodiments, the barcode sequence is 4 to 250 nucleotides long, or any sub-range therein, as described above.

In some embodiments, the first and/or second oligonucleotide further comprises one or more of: a uracil base; a biotin base; or an adapter sequence for sequencing reactions.

In some embodiments, the composition comprises a partition described herein. The partition can comprise two or more, or multiple, barcoded solid supports described herein, where each solid support is linked or attached to a different oligonucleotide (a solid support oligonucleotide). In some embodiments, the solid support oligonucleotide comprises a barcode unique for the solid support to which it is attached. In some embodiments, the partition comprises a first solid support attached to a first solid support oligonucleotide comprising a first barcode unique for the first solid support, and a second solid support attached to a second solid support oligonucleotide comprising a second barcode unique for the second solid support.

In some embodiments, the partition comprises two or more, or multiple, solid supports, where each solid support is linked or attached to two or more different oligonucleotides, where the two or more oligonucleotides can comprise: (i) a first oligonucleotide comprising a barcode unique for the solid support, a capture sequence, and a sequencing adaptor; and (ii) a second oligonucleotide comprising a barcode unique for the solid support, a sequencing adaptor, and a palindrome sequence at the 3' end. In some embodiments, the second oligonucleotide also comprises a capture sequence.

In some embodiments, the partition comprises two or more solid supports, wherein each solid support is linked to (i) a plurality of first solid support oligonucleotides comprising a barcode sequence unique for the solid support and a capture sequence; and (ii) a plurality of second oligonucleotides having a 3' end comprising a sequence complementary to the capture sequence, the barcode sequence, and a 5' palindromic sequence. In some embodiments, the first solid support oligonucleotides and the second oligonucleotides comprise the same barcode sequence.

In some embodiments, the partition comprises additional components for synthesis or amplification of nucleic acids sequences, such as transposases, R2 retrotransposases, reverse transcriptases, polymerases, ligases, UDGases, or tagmentases, nucleotides such as dNTPs, primers, buffers, divalent ions, and salts.

In some embodiments, the partition comprises reagents for adding polynucleotide tails to RNA molecules, such as 3' poly(A) tails. The reagents can include poly(A) polymerase and ATP. In some embodiments, the partition comprises reagents for fragmenting RNA, such as RNAse H and random primers. The random primers can be blocked to prevent extension by enzymes such as polymerases, transcriptases, or retrotransposases.

In some embodiments, the solid support is a bead or magnetic bead.

Also provided are reaction mixtures comprising two or more, or multiple, barcoded solid supports described herein, where each solid support is linked or attached to a different oligonucleotide (a solid support oligonucleotide). In some embodiments, the solid support oligonucleotide comprises a barcode unique for the solid support to which it is attached. In some embodiments, the reaction mixture comprises additional components for synthesis or amplification of nucleic acids sequences, such as transposases, reverse transcriptases, polymerases, ligases, UDGases, or tagmentases, nucleotides such as dNTPs, primers, buffers and salts. In some embodiments, the solid support is a bead or magnetic bead.

Also provided are kits comprising two or more, or multiple, barcoded solid supports described herein, where each solid support is linked or attached to a different oligonucleotide (a solid support oligonucleotide). In some embodiments, the solid support oligonucleotide comprises a barcode unique for the solid support to which it is attached. In some embodiments, the kit comprises additional components for synthesis or amplification of nucleic acids sequences, such as transposases, reverse transcriptases, polymerases, ligases, UDGases, or tagmentases, nucleotides such as dNTPs, primers, buffers and salts. In some embodiments, the solid support is a bead or magnetic bead. In some embodiments, the kit comprises instructions for use of the components of the kit by an end user.

Methods of Producing a Solid Support

Also provided are methods of producing a solid support, the method comprising attaching an oligonucleotide to the solid support, wherein the oligonucleotide comprises a barcode sequence unique to the solid support. In some embodiments, the oligonucleotide is chemically conjugated to the solid support. In some embodiments, the oligonucleotide is non-covalently attached to the solid support. In some embodiments, the oligonucleotide comprises a nucleic acid sequence having a universal tag or primer sequence, a barcode sequence, and an oligo dT sequence. In some embodiments, the oligonucleotide further comprises a capture sequence linked to a detector oligonucleotide having a 3' end complementary to the capture sequence and a 5' palindromic sequence.

In some embodiments, the method for producing a solid support linked to an oligonucleotide comprises:

i) providing a solid support linked to a plurality of first solid support oligonucleotides, the first oligonucleotides comprising a barcode sequence unique for the solid support and a 3' capture sequence;

ii) hybridizing the 3' capture sequence of some of the solid support oligonucleotides to a second oligonucleotide having a 3' end comprising a sequence complementary to the capture sequence, and a 5' palindromic sequence, wherein the ratio of first solid support oligonucleotides to second oligonucleotide is at least 5:1, 10:1, 100:1, 1000:1, 5000:1, 10000:1, 20000:1; 30000:1. 40000:1, 50000:1; 60000:1, 70000:1; 80000:1, 90000:1, or 100000:1;

iii) extending the first solid support oligonucleotides with a polymerase to generate extended solid support oligonucleotides that comprise a complement of the second oligonucleotide and a 3' end that is complementary to the palindromic sequence; thereby producing the solid support.

In some embodiments, the first oligonucleotides comprise a uracil base 5' of the barcode sequence, and the extended solid support oligonucleotides from step (iii) are released from the solid support by UDGase. In some embodiments, the partition comprises UDGase, and the extended solid support oligonucleotides from step (iii) are released from the solid support inside the partition.

In some embodiments, the second oligonucleotides are removed by denaturation and washing. In some embodiments, the second oligonucleotides are removed by denaturation during the first amplification cycle, for example during the first PCR cycle. In some embodiments, the denaturation occurs inside a partition. In some embodiments, the second oligonucleotides are removed by denaturation prior to the solid supports being added to the partitions.

EXAMPLES

Example 1

This example provides the reaction mixtures for generating partitions, in this case droplets, and reverse transcription to produce chimeric barcodes described herein.

| Barcode suspension mix | | |
| --- | --- | --- |
| Components | 1× vol ul | 2× vol |
| 3' Barcode Mix (5000 b/ul) | 50 | 105 |
| Barcode Buffer (v1) | 50 | 105 |
| Total | 100 | 210 |

| Cell suspension mix | | |
| --- | --- | --- |
| Components | 1× vol ul | 4.8×vol |
| Cell suspend Buffer (v2) | 41.9 | 201.12 |
| DTT | 6.7 | 32.16 |

-continued

| | | |
|---|---|---|
| 3' Enzyme Mix | 15.4 | 73.92 |
| RTase | 11 | 52.8 |
| Cells in PBS/BSA 1200/ul | 16.66 + 8.34 | 120 |
| Total | 100 | 480 |

Droplet generation

1. Prime the big chip with 50 ul prime solution.
2. Add 100 ul of cell suspension mix into each cell well.
3. Add 100 ul of bead solution into each bead well.
4. Load 700 ul of oil into each oil well.
5. Put the gasket on, loac the chip onto the DG, start droplet generation.
6. Collect droplet into 96-well ddPCR plate.

1-step RT/SSS incubation and Ampure cleanups

1. Dropletize Barcode and Cell Suspension Mix, transfer 100 ul emulsion/oil per well in PCR plate.
2. Run RT @ 50 C. for 45 min, set volume on C1000 at 125 ul.
3. Run BST @ 70 C. for 45min.
4. Heat inactive RT and BST @ 85 C. for 5 min.
5. Pool all wells from 1 sample into 1.5 ml lobind tube. Remove oil leaving ~20ul behind. Add 50 ul Droplet Disrupter per well.
6. Remove 50 ul oil/droplet disruptor from bottomof tube.
7. Add 200 ul water + 230 ul Ampure XP. (10 min bind, 10 min magnet, 2 EtOH washes, 5 min dry, 2 min elute, 2 min magent.)
8. Elute samples in 100 ul RSB + 0.05% Tween20.
9. Add 60 ul Ampure XP into each sample for second cleanup. (5 min bind, 5 min magnet, 2 EtOH washes, 2 min elute, 2 min magnet.)
10. Elute samples in 11 ul RSB.
11. Run 1 ul cDNA on Bioanalyzer.
12. Continue with Tagmentation, PCR, final cleanups and library quantification.
06082018_V2_Tag_Bigchip_Hek/3T3_10k_Tagment&Nxtera
Tagmentation and PCR from (Surecell v1 protocol)

| Tagment Mix | | |
|---|---|---|
| Components | 3-10 ng cDNA | 11-20 ng cDNA |
| cDNA | 10 | 10 |
| Z-carrier DNA (5 ng/ul) | 0 | 0 |
| 5× Tagment Buffer | 8 | 8 |
| v1 Tagment Enzyme | 10 | 20 |
| Nuclease-free water | 12 | 2 |
| Total | | |

Incubate tagment rxn at 55 C. for 5 min and hold at 4 C.
Remove the plate immediately when temp reaches 4 C., do not leave at 4 C. longer than 5 min
Add 10 ul Tagment Stop Buffer, mix and spin down, let sit at RT for 5 min fefore assemling PCR mix.

| PCR mix | |
|---|---|
| Components | 1× vol (ul) |
| Tagmented cDNA | 50 |
| Tagment PCR Mix or NPM | 30 |
| P5-Oligo Hybrid PCR primer (5 um) | 10 |
| N70× index primer (5 uM) | 10 |
| Total | 100 |

| PCR cycling protocol (Eureka) | | |
|---|---|---|
| 95° C. | 30 sec | |
| 95° C. | 10 sec | 15 cycles for low cell input (<2000 cells) |
| 60° C. | 45 sec | 12 cycles for high cell input (>5000 cells) |
| 72° C. | 60 sec | |
| 72° C. | 5 min | |
| 4° C. | hold | |

Example 2

This Example described formation of barcode oligos chimeras in single-cell total RNA library preparation workflow.

Cell Preparation. K-562 cells (ATCC, CCL-243) and NIH3T3 cells (ATCC, CRL-1658) were used for ddSEQ reagents setup. Cells were harvested from T75 flasks and washed 3 times with cold 1× PBS+0.1% BSA solution before cell count on Bio-Rad's TC20 Cell Counter. Following cell count, cells were diluted to a final concentration of 300 cells/μl in 1×PBS+0.1% BSA solution. K-562 and NIH3T3 cells were mixed in a 1:1 ratio for the experiment.

Single-Cell Isolation and Barcoding. Cell and Bead suspension mixes were prepared before loading in the SureCell ddSEQ M cartridge (Biorad, PN12008720). The composition of the Cell suspension mix includes Tris buffer, salts, dNTPs, 5' and 3' adaptor primers, detergent, density gradient media, enzymes mix, DNA polymerase, and 52 cells/μl K-562/NIH3T3 cells. The Bead suspension mix contains Tris buffer, salts, ATP, detergents, density gradient media, enzyme, and 10,000 barcoded beads/μl (note: barcoded bead consists of 2 oligo types, 3' poly(dT) and 3' palindromic sequence). 20 μl each of Cell suspension mix and Bead suspension mix, and 80 μl Encapsulation oil were dispensed into corresponding labeled wells in the SureCell ddSEQ M cartridge. The cartridge was loaded into the ddSEQ Single Cell Isolator (Bio-Rad, PN 12004336) and ran for approximately 5 minutes to form emulsions of combined cell and bead in droplets.

The emulsion droplets were transferred to a Bio-Rad's ddPPCR 96-well plate and sealed using an 8-cap strip. Droplets incubation was carried out in a Bio-Rad's C1000 Touch Thermal Cycler and set at 37° C. for 30 min, 94° C. for 2 min, 59° C. for 2 min, 72° C. for 2 min, 95° C. for 30 sec, 48° C. for 1 min, 72° C. for 2 min, ramp down to 4° C. at 0.1 C/s and hold at 4° C. for 15 minutes.

Library Preparation. Contents of the emulsion droplets were released by adding 40 μl droplet disruptor to each sample. Unbound dT tails from bead oligos were blocked with excess Poly(dA). Barcoded captured RNAs were reversed transcribed and 3' adapter added-on in a 100 μl reaction containing Tris buffer, salts, dNTPs, 3' adapter oligos, RNase inhibitor, and 2Dzyme. The reaction was incubated at 34 C for 1 hour in a Bio-Rad's C1000 Touch Thermal Cycler. The cDNA library was then purified using 80 μl Agencourt Ampure XP beads following the manufacturer's instructions.

The purified cDNA was amplified and sample indexed in a 50 μl volume that included Kapa HiFi HotStart Ready Mix, and Nextera P5 and P7 index primers. PCR was performed in a Bio-Rad's C1000 Touch Thermal Cycler with an initial denaturation step at 95° C. for 3 min and cycling conditions of 98° C. for 20 s, 60° C. for 45 s, and 72° C. for 60 s, for 12 cycles and 72° C. for 5 min for the last cycle. PCR products were size selected and purified with 40 μl Agencourt Ampure XP beads. The final DNA library was analyzed and quantified on an Agilent Bioanalyzer before sequencing.

Sequencing. The DNA library was sequenced in Illumina's NextSeq system using the NextSeq 500/550 high output kit (150 cycles). The library was loaded into the system at 1.8 pM final concentration and the run was set to 54 cycles for Read 1, 75 cycles for Read 2, and 8 cycles for Index 1.

Analysis. Sequencing data was analyzed using Bio-Rad's internal scRNAseq pipeline. The analysis and results are summarized in the following figures.

Figures 12A, 12B:
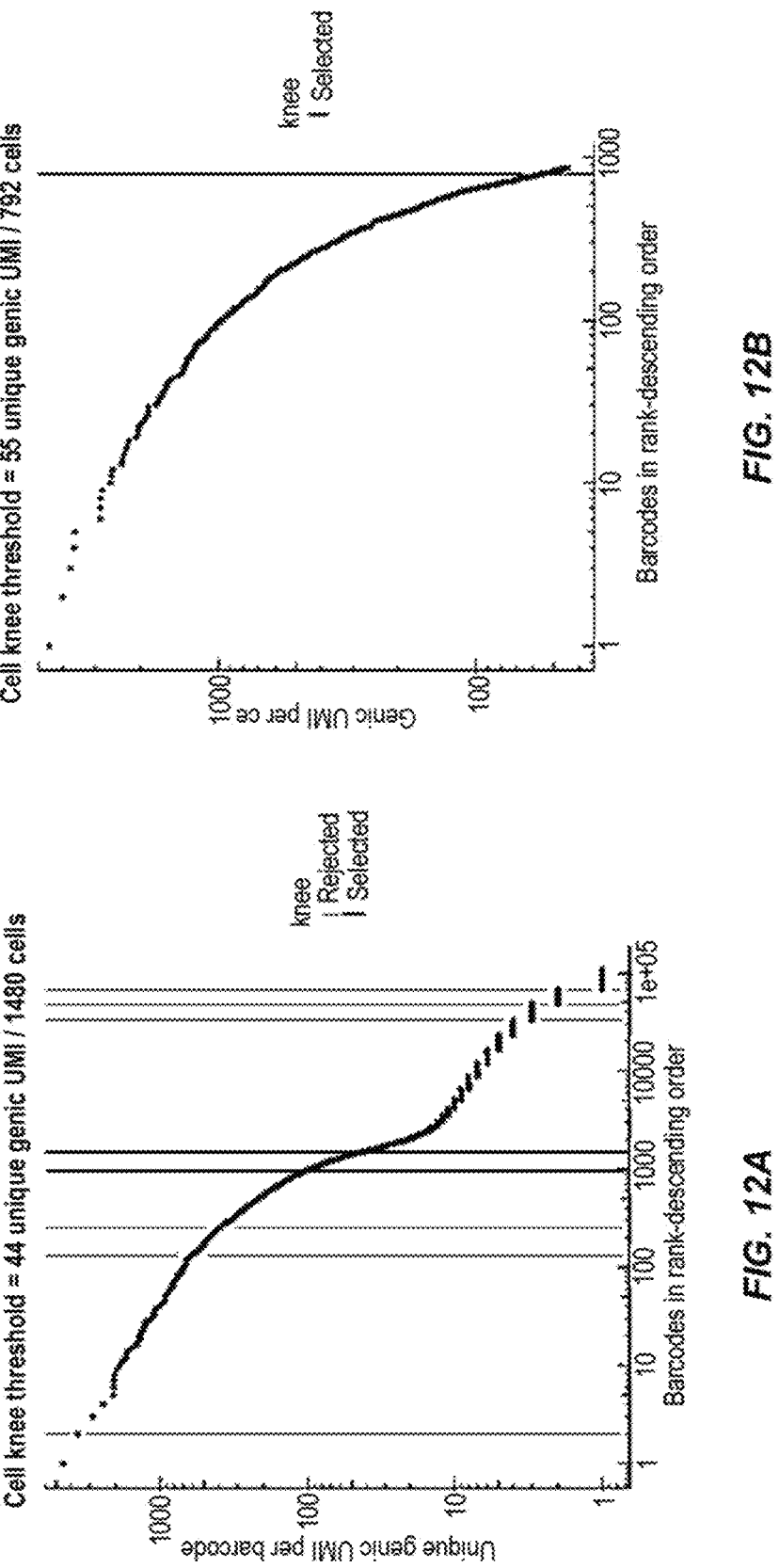
FIGS. 12A and 12B show representative data produced by the methods described herein.
Figure 13:
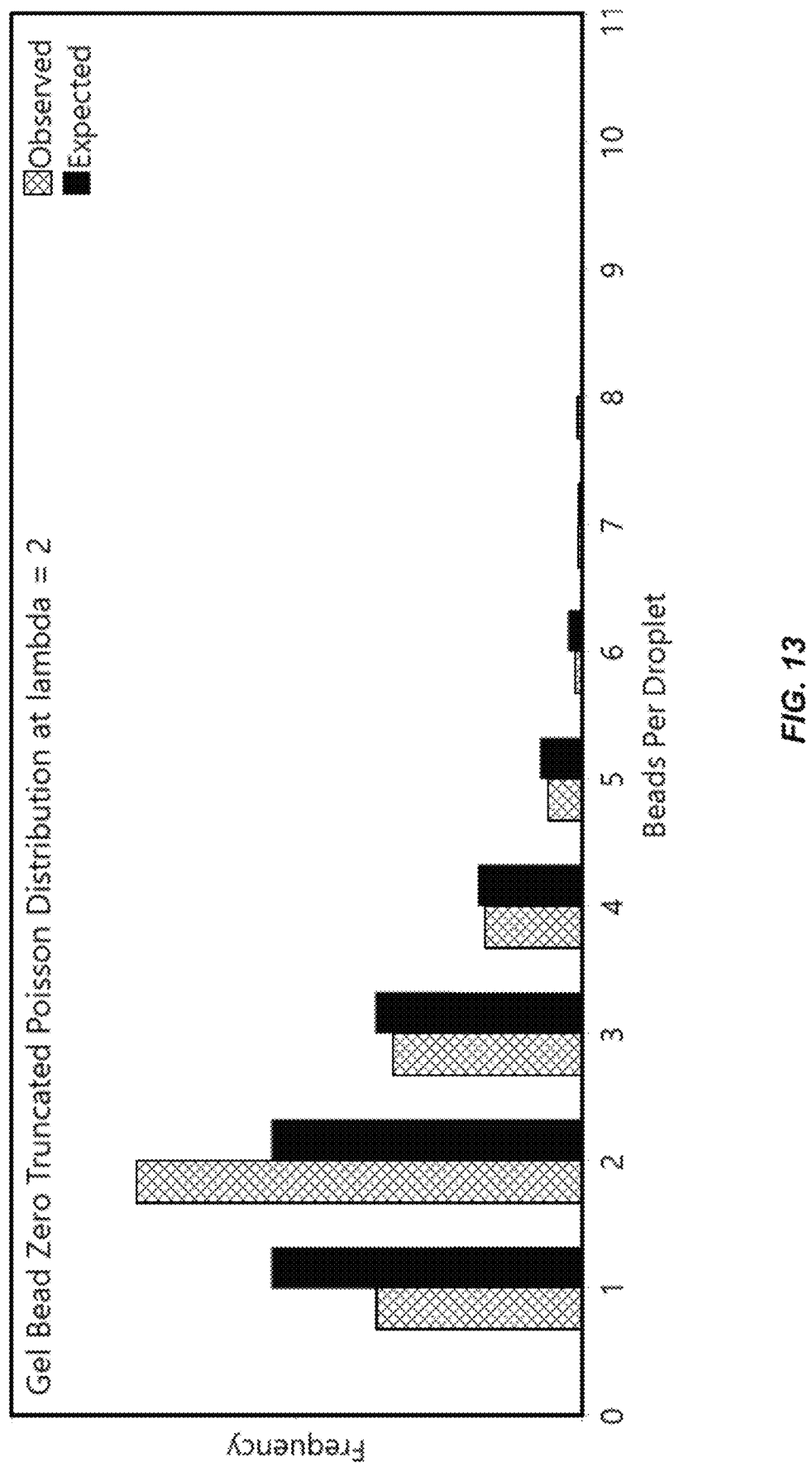
FIG. 13 shows the theoretical expected #of beads per droplet as calculated from the bead concentration and the droplet size. The observed #of beads in droplets are provided by the deconvolution based on NGS data of the number of bead barcodes co-localizing to discrete droplets. The observed number of barcodes matches closely the expected, with the exception of a greater number of bead doublets and a lower than expected number of singlets. These data demonstrate the feasibility of using the methods and compositions described herein to co-localize beads to discrete droplets.
Figure 14:
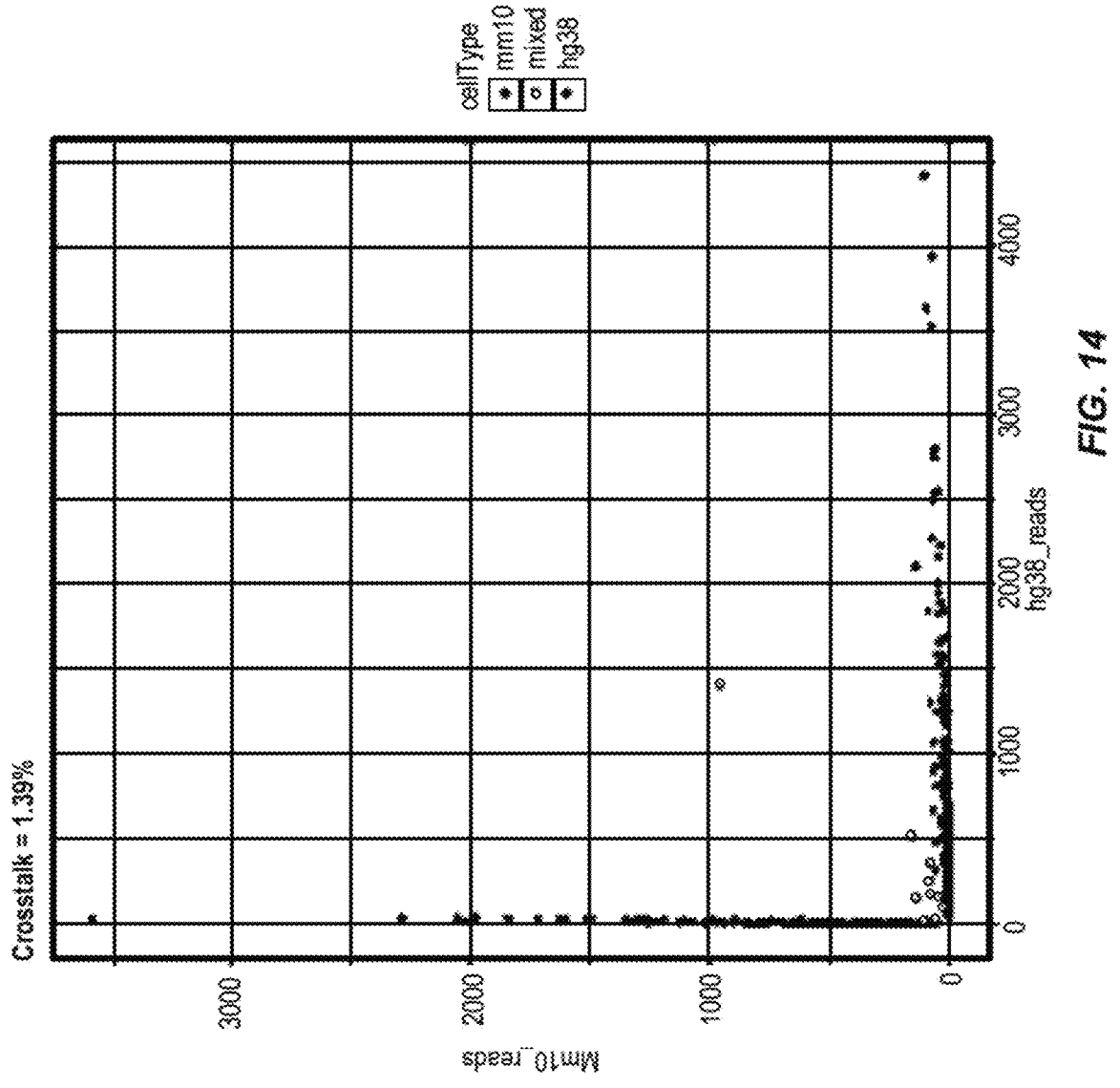
FIG. 14 shows a 2D plot of human K562 and mouse 3T3 single cell NGS data after bead deconvolution and merging mapping to either the human (hg38) or mouse (min10) coding sequences. The number of reads per merged single cell data point is shown on the X and Y axes. Crosstalk, defined by K562 (hg38) and 3T3 (mm10) cells co-localizing to discrete droplets was calculated as 1.39%. This demonstrates that compositions and methods described herein generate single cell data and that bead co-localization is accurate, which is inferred by little to no inadvertent merging of mouse and human data.

Results: The total number of cells input into the sample was 1040 (52 cells/ul×20 ul). The number of cells called before bead merging was 1480 (FIG. 12A) and the number of cells called after bead merging was 792 (FIG. 12B). The data showed bead merging was functional and effective. The cell recovered, 76%, was consistent with the cell input and expected yield. The observed and expected bead distributions also closely match each other (FIG. 14), and support the effectiveness of barcode merging. Overall, the results demonstrated that bead barcode deconvolution can be achieved by the method employed in this example.

Example 3

This Example described bead barcode oligo concatemer formation using R2 retrotransposase in droplets.

R2 retrotransposase was used to generate heterodimers in the 3'WTA library for bead deconvolution. The workflow is illustrated in FIG. 16. After encapsulating cells and beads (step 1), R2 retrotransposase is added to the compartmentalized reaction (step 2), and forms concatemer prior to reverse transcription and second strand synthesis. Magnetic bead size separation during purification (step 3) generates small size fraction (<300 bp) and large size fraction (>300 bp). The workflow then splits into the small fraction (<300 bp) (steps 4,6,7) and large fraction (>300 bp) (step 5). Each fraction is processed independently for sequencing library generation and combined prior to loading onto the sequencer. The R2 retrotransposase formed dimers are used for bioinformatics bead deconvolution.

Although the foregoing disclosure has been described in some detail by way of illustration and example for purposes of clarity of understanding, one of skill in the art will appreciate that certain changes and modifications may be practiced within the scope of the appended claims. In addition, each reference provided herein, including patents, patent applications, non-patent literature, and Genbank accession numbers, is incorporated by reference in its entirety to the same extent as if each reference was individually incorporated by reference.

Where a conflict exists between the instant application and a reference provided herein, the instant application shall dominate.

What is claimed is:

1. A method for producing a library for sequencing, the method comprising:

encapsulating a single cell and multiple solid supports within a partition, wherein each solid support is linked to (i) first oligos that include a barcode unique to the solid support, a sequencing adaptor, and a 3' capture sequence, and (ii) second oligos that include the barcode unique to the solid support, a sequencing adaptor, and a 3' palindrome sequence common to the second oligos;

lysing the cell in the partition;

releasing the first oligos and the second oligos from the solid support;

hybridizing the first oligos to RNA from the single cells;

hybridizing the 3' palindrome sequences of the second oligos to each other and extending the hybridized second oligos to form DNA dimers;

releasing the contents of the partitions;

extending the hybridized first oligos with an R2 retrotransposon to synthesize cDNA in the presence of an acceptor template to add a 3' adaptor sequence;

amplifying the DNA dimers and the cDNA to yield a library comprising adaptor sequences; and sequencing the library to produce sequence reads, wherein barcodes in a sequence read indicate solid supports that were present in the partition.

2. The method of claim 1, further comprising fragmenting the RNA to produce RNA fragments before hybridizing the RNA from the single cells to the capture sequence.

3. The method of claim 1, wherein the partition comprise a DNA polymerase, divalent ions, deoxynucleotide triphosphates (dNTPs), and primers.

4. The method of claim 2, wherein the partition further comprises poly(A) polymerase and ATP, and a poly-A tail is added to the RNA fragments.

5. The method of claim 1, wherein each of the first and second oligos comprises a uracil base, and the releasing step uses a UDGase or USER enzyme.

6. The method of claim 1, further comprising melting double stranded DNA molecules of the library and hybridizing primers to the adaptor sequences, extending the primers using a polymerase to form an extended molecule, and amplifying the extended molecule by PCR.

7. The method of claim 1, wherein the capture sequence comprises poly dT, a random sequence, or a gene-specific sequence.

8. The method of claim 1, wherein the partition is a microwell or a droplet in an emulsion.

9. A method for detecting multiple beads, the method comprising:

encapsulating a cell and multiple beads into a partition, wherein each bead is attached to (i) first oligos that have a barcode sequence unique to the bead and 3' RNA
capture sequences and (ii) second oligos that have the
barcode sequence and a 3' palindrome sequence com-
mon to the second oligos;
releasing the first oligos and second oligos from the
beads;
releasing RNA from the cell;
making cDNA copies of the RNA using the first oligos;
hybridizing the 3' palindrome sequences of the second
oligos with each other and extending to form DNA
dimers;
sequencing the cDNA and the DNA dimers to produce
sequence reads; and
identifying barcodes together in the sequence reads.

\* \* \* \* \*

48

SEQUENCE LISTING

```
<160> NUMBER OF SEQ ID NOS: 9

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
```

-continued

```
       oligonucleotide

<400> SEQUENCE: 1
agatgtgtat aagagacag                                                  19

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ctgtctctta tacacatct                                                  19

<210> SEQ ID NO 3
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tcgtcggcag cgtc                                                       14

<210> SEQ ID NO 4
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gtctcgtggg ctcgg                                                      15

<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tcgtcggcag cgtcagatgt gtataagaga cag                                  33

<210> SEQ ID NO 6
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gtctcgtggg ctcggagatg tgtataagag acag                                34

<210> SEQ ID NO 7
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide
```

-continued

```
<400> SEQUENCE: 7
actcgctata gccaatctga acgcctatgc atgacaacca cacagtcagt cacggctgct      60
t                                                                      61

<210> SEQ ID NO 8
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
actcgctacg cggaattctg aacgcctatg catgacaacc acacagtcag tcaaggcttc      60
tttttttttt tttttttttt ttt                                              83

<210> SEQ ID NO 9
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(15)
<223> OTHER INFORMATION: a, c, t, g, unknown or other
<220> FEATURE:
<221> NAME/KEY: modified_base
<222> LOCATION: (29)..(35)
<223> OTHER INFORMATION: a, c, t, g, unknown or other
<220> FEATURE:
<221> NAME/KEY: modified_base
<222> LOCATION: (46)..(52)
<223> OTHER INFORMATION: a, c, t, g, unknown or other

<400> SEQUENCE: 9
nnnnnnnnnn nnnnnvgcta tgcatgacnn nnnnncagtc agtcannnnn nnttttt          57
```